US010052596B2

(12) United States Patent
Richardson

(10) Patent No.: US 10,052,596 B2
(45) Date of Patent: Aug. 21, 2018

(54) APPARATUS AND METHOD FOR LIQUIDS AND GASES

(71) Applicant: Gaia USA, Inc., Scottsdale, AZ (US)

(72) Inventor: Thomas A. Richardson, Victoria (CA)

(73) Assignee: Gaia USA, Inc., Scottsdale, AZ (US)

( * ) Notice: Subject to any disclaimer, the term of this patent is extended or adjusted under 35 U.S.C. 154(b) by 252 days.

(21) Appl. No.: 14/573,300

(22) Filed: Dec. 17, 2014

(65) Prior Publication Data

US 2015/0202579 A1 Jul. 23, 2015

Related U.S. Application Data

(60) Provisional application No. 61/918,811, filed on Dec. 20, 2013.

(51) Int. Cl.
*B01F 5/06* (2006.01)
*B01F 3/04* (2006.01)
(Continued)

(52) U.S. Cl.
CPC .......... *B01F 5/0614* (2013.01); *B01F 3/0446* (2013.01); *B01F 3/04524* (2013.01); *B01F 5/0415* (2013.01); *B01F 5/0428* (2013.01); *B01F 5/0451* (2013.01); *B01F 5/0463* (2013.01); *B01F 5/0473* (2013.01); *B01F 5/0476* (2013.01); *B01F 5/0485* (2013.01); *B01F 5/106* (2013.01);
(Continued)

(58) Field of Classification Search
CPC .............. B01F 3/04099; B01F 3/04262; B01F 3/04525; B01F 5/0614; B01F 5/0415; B01F 5/0428; B01F 5/0451; B01F 5/0463; B01F 5/0473; B01F 5/0476; B01F 5/0485; B01F 5/106; B01F 13/1016
See application file for complete search history.

(56) References Cited

U.S. PATENT DOCUMENTS 2,601,018 A 6/1952 Heyl et al.
3,452,966 A 7/1969 Smolski
(Continued)

FOREIGN PATENT DOCUMENTS

CN 87201156 U 12/1987
GB 1254179 A 11/1971
(Continued)

OTHER PUBLICATIONS

PCT/US2014/070813. Applicant: Gaia, USA Inc. Int'l Search Report & Written Opinion (dated Apr. 28, 2015).

*Primary Examiner* — David G Cormier
(74) *Attorney, Agent, or Firm* — Loza & Loza, LLP; David S. Sarisky

(57) ABSTRACT

Aspects of the present disclosure provide various apparatus and methods. In some embodiments, an apparatus is provided for mixing a gas with a liquid. The apparatus may include a pipe having two ends. The pipe may provide a main fluid path and may have an interior surface having a first groove. The apparatus may also include a helical vane disposed inside the pipe. The vane may have a first projecting tongue that engages the first groove. The apparatus may also include a gas injection port on the pipe adapted to inject gas into the fluid path upstream of the helical vane. In some embodiments, the helical vane may be a 3D printed component.

13 Claims, 19 Drawing Sheets

(51) Int. Cl.
| | |
|---|---|
| *B01F 15/00* | (2006.01) |
| *B08B 3/10* | (2006.01) |
| *B29C 67/00* | (2017.01) |
| *B01F 5/04* | (2006.01) |
| *B01F 5/10* | (2006.01) |
| *C12M 1/00* | (2006.01) |
| *B01F 13/00* | (2006.01) |
| *B01F 13/10* | (2006.01) |
| *B33Y 10/00* | (2015.01) |
| *B01F 5/00* | (2006.01) |
| *B29L 23/00* | (2006.01) |

(52) U.S. Cl.
CPC ...... *B01F 13/0049* (2013.01); *B01F 13/1016* (2013.01); *B01F 15/0022* (2013.01); *B01F 15/00558* (2013.01); *B08B 3/10* (2013.01); *B29C 67/0055* (2013.01); *C12M 1/00* (2013.01); *B01F 2003/04879* (2013.01); *B01F 2003/04893* (2013.01); *B01F 2003/04943* (2013.01); *B01F 2005/0094* (2013.01); *B01F 2005/0638* (2013.01); *B01F 2201/00* (2013.01); *B01F 2215/008* (2013.01); *B01F 2215/0427* (2013.01); *B29L 2023/00* (2013.01); *B33Y 10/00* (2014.12)

(56) References Cited

U.S. PATENT DOCUMENTS

| | | |
|---|---|---|
| 3,852,384 A | 12/1974 | Bearden |
| 3,953,002 A | 4/1976 | England, Jr. et al. |
| 4,088,449 A | 5/1978 | Smith |
| 4,127,332 A | 11/1978 | Thiruvengadam et al. |
| 4,202,635 A | 5/1980 | Hendrickson |
| 4,408,893 A | 10/1983 | Rice, III |
| 4,466,741 A | 8/1984 | Kojima |
| 4,674,888 A * | 6/1987 | Carlson ............... B01F 3/04262 162/57 |
| 4,749,527 A | 6/1988 | Rasmusen |
| 4,761,077 A * | 8/1988 | Werner ............... B01D 19/0057 137/896 |
| 4,767,026 A | 8/1988 | Keller et al. |
| 4,872,833 A | 10/1989 | Kramer |
| 5,498,078 A | 3/1996 | Keller |
| 5,842,600 A | 12/1998 | Singleterry et al. |
| 5,935,490 A * | 8/1999 | Archbold ............... B01F 3/0446 261/76 |
| 6,039,884 A | 3/2000 | Burris et al. |
| 6,923,568 B2 | 8/2005 | Wilmer et al. |
| 7,103,450 B2 | 9/2006 | Kubiak et al. |
| 7,772,376 B2 | 8/2010 | Payne et al. |
| 7,814,745 B2 | 10/2010 | Levin et al. |
| 7,905,653 B2 | 3/2011 | Wilmer et al. |
| 7,975,991 B2 | 7/2011 | Kojima |
| 8,177,197 B1 | 5/2012 | Ergican |
| 8,272,777 B2 | 9/2012 | Kohrs et al. |
| 8,286,951 B2 | 10/2012 | Dart et al. |
| 8,371,114 B2 | 2/2013 | Hayashi et al. |
| 2001/0033526 A1 | 10/2001 | Illy et al. |
| 2004/0112404 A1* | 6/2004 | Doke ................. B01F 3/04269 134/1.3 |
| 2004/0124136 A1 | 7/2004 | Bak |
| 2005/0155922 A1 | 7/2005 | Tormaschy et al. |
| 2006/0120214 A1 | 6/2006 | Raftis |
| 2008/0062813 A1 | 3/2008 | Wilmer et al. |
| 2008/0237140 A1 | 10/2008 | Liverud et al. |
| 2009/0034361 A1 | 2/2009 | Trang et al. |
| 2009/0308472 A1 | 12/2009 | Harman |
| 2010/0031825 A1 | 2/2010 | Kemp |
| 2010/0208547 A1 | 8/2010 | Kiel et al. |
| 2011/0153084 A1 | 6/2011 | Wilmer et al. |
| 2012/0195994 A1* | 8/2012 | El-Siblani ............ B29C 67/007 425/174.4 |

FOREIGN PATENT DOCUMENTS

| | | |
|---|---|---|
| WO | 95/12452 A2 | 5/1995 |
| WO | WO2013050764 | 4/2013 |

* cited by examiner

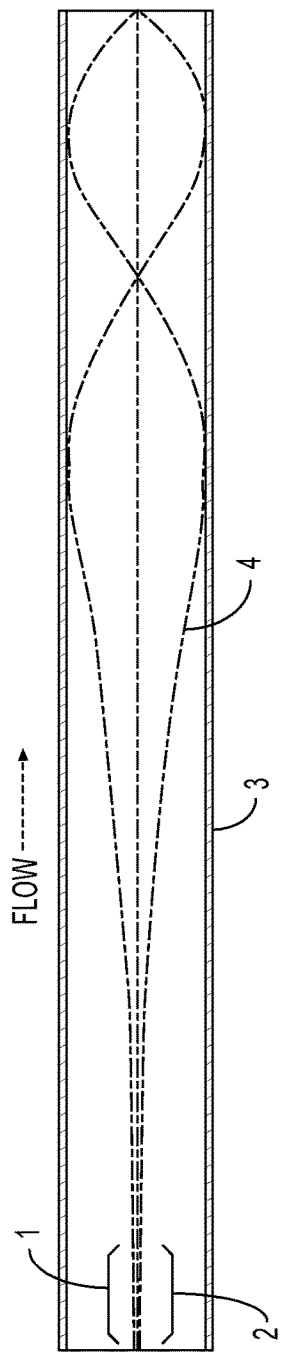
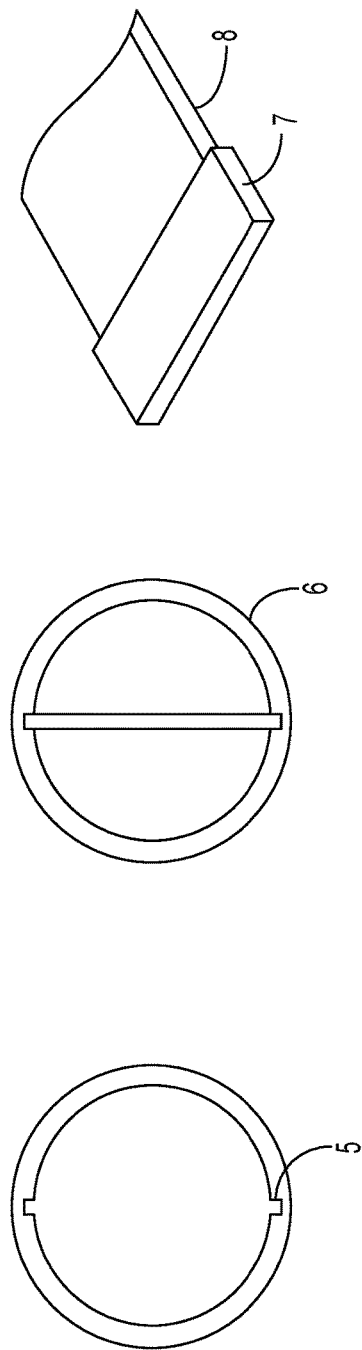
FIG. 1A  FIG. 1B  FIG. 1C  FIG. 1D

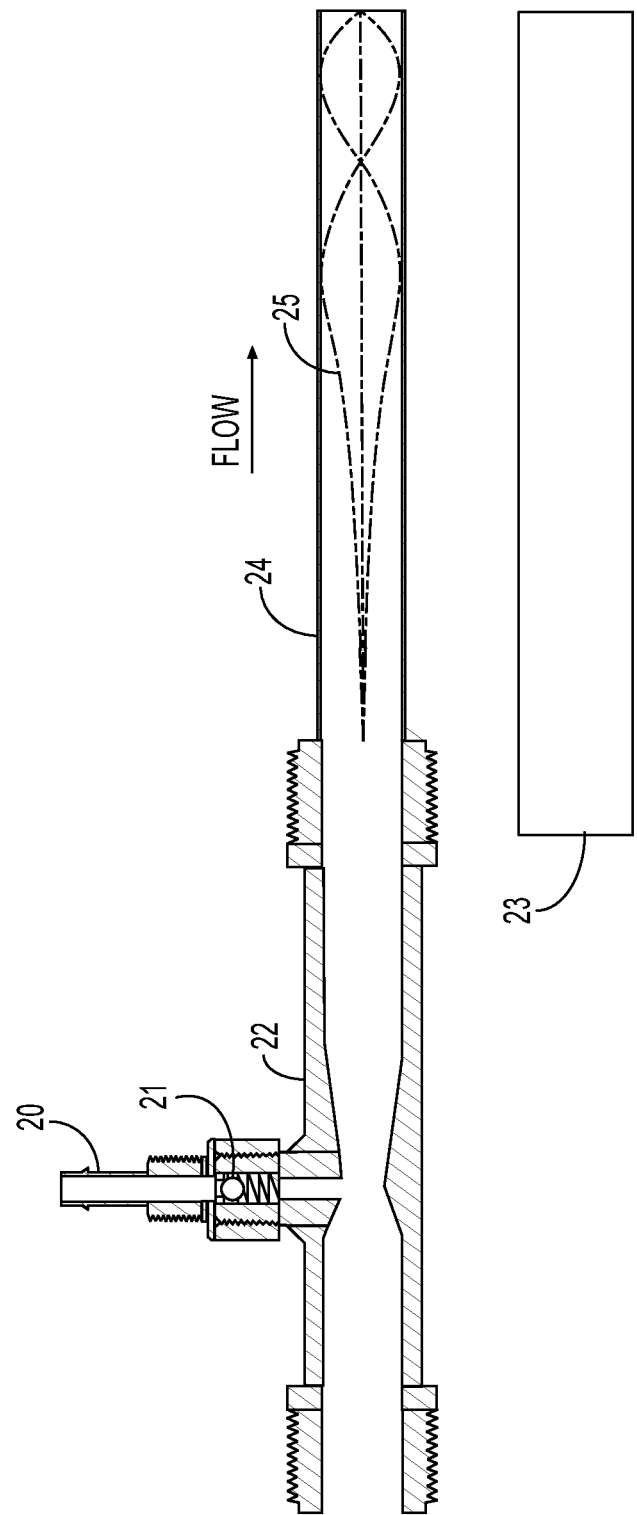

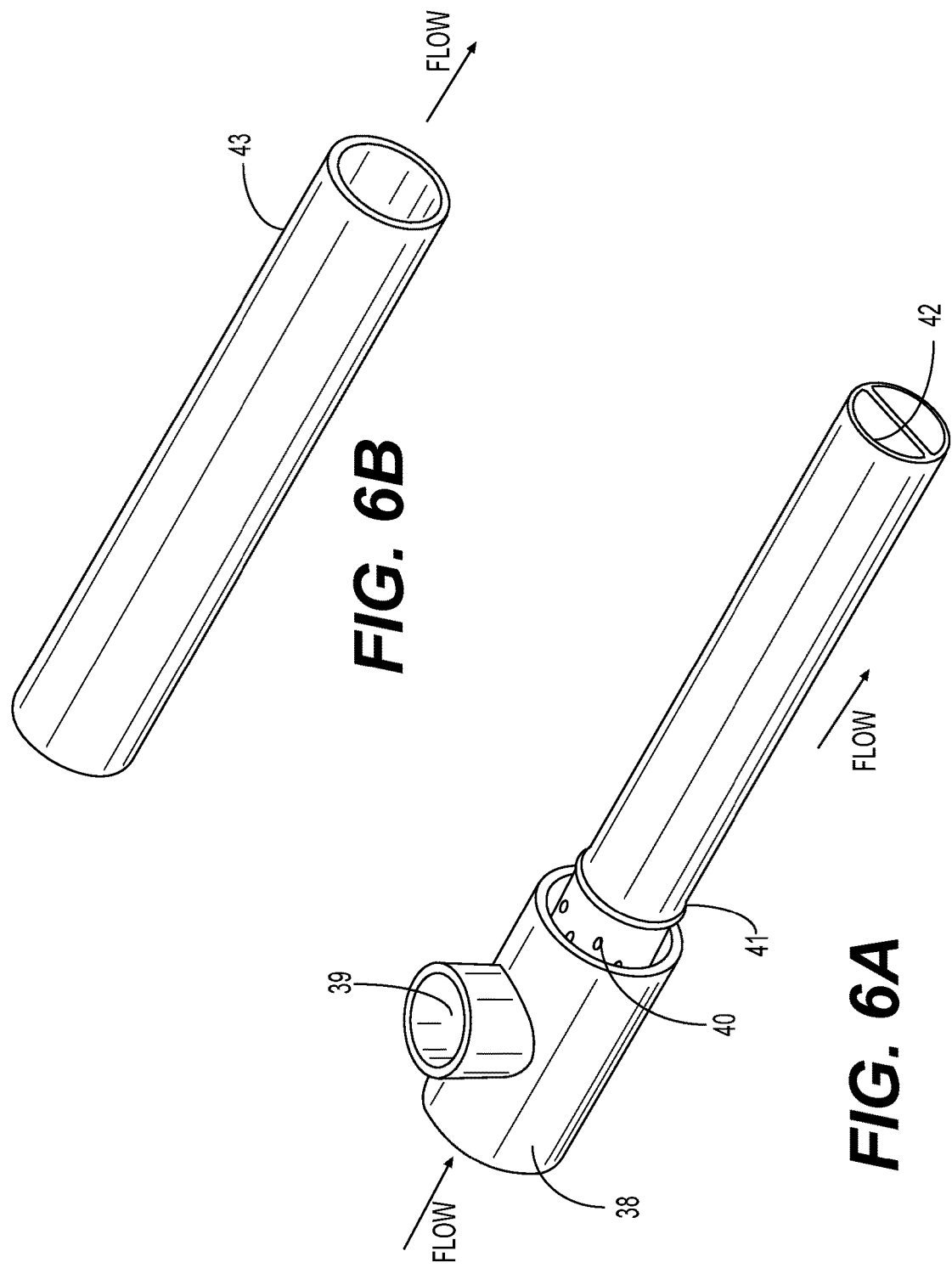

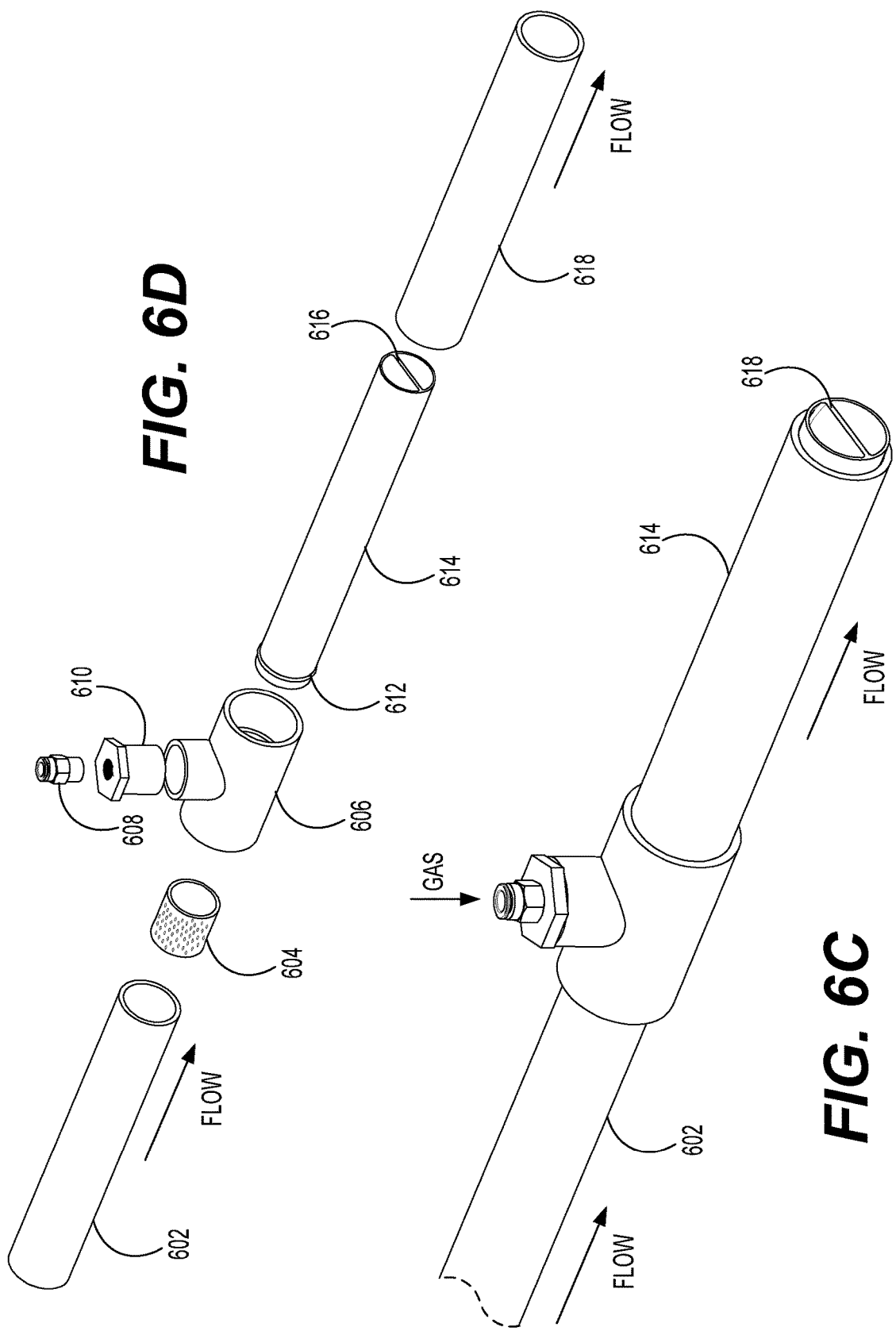

APPARATUS AND METHOD FOR LIQUIDS AND GASES

CROSS-REFERENCE TO RELATED APPLICATION(S)

This application claims priority to and the benefit of provisional patent application No. 61/918,811, filed in the United States Patent and Trademark Office on Dec. 20, 2013, the entire content of which is incorporated herein by reference as if fully set forth below and for all applicable purposes.

TECHNICAL FIELD

Aspects of the present disclosure relates to liquid and/or gas systems and methods.

BACKGROUND

U.S. Pat. No. 4,749,527, issued Jun. 7, 1988, describes a Static Aerator. International Patent Publication No. WO 1995012452 A2, published May 11, 1995, describes a Gas Injection Method and Apparatus.

SUMMARY

The following presents a simplified summary of one or more aspects of the present disclosure, in order to provide a basic understanding of such aspects. This summary is not an extensive overview of all contemplated features of the disclosure, and is intended neither to identify key or critical elements of all aspects of the disclosure nor to delineate the scope of any or all aspects of the disclosure. Its sole purpose is to present some concepts of one or more aspects of the disclosure in a simplified form as a prelude to the more detailed description that is presented later.

Aspects of the present disclosure provide various apparatus and methods. Some aspects of the present disclosure provide for an apparatus that mixes a gas with a liquid. The apparatus may include a pipe having two ends, with a first end being a liquid input end and a second end being a liquid outlet end. The pipe may provide a main fluid path. The pipe may have an interior surface having a first groove disposed thereon. A helical vane may be disposed inside the pipe, dividing a portion of the fluid path into two fluid path regions. The vane may have a first projecting tongue that engages the first groove. The apparatus may also include a gas injection port on the pipe adapted to inject gas into the fluid path upstream of the helical vane. In some embodiments, the tube and the helical vane are unitary with each other.

Some aspects of the present disclosure provide for a method of manufacturing an apparatus for mixing a gas with a liquid. The method may include programming a three-dimensional (3D) printer to print a mixing assembly having desired characteristics. The method may also include programming the 3D printer to print the mixing assembly with the 3D printer. The desired characteristics of the mixing assembly may include a tube having two ends, with a first end being a liquid input end and a second end being a liquid outlet end. The tube may provide a main fluid path. The desired characteristics may also include a helical vane disposed inside the tube, dividing a portion of the fluid path into two fluid path regions. The desired characteristics may also include a gas injection port on the tube adapted to inject gas into the fluid path upstream of the helical vane.

Some aspects of the present disclosure provide for a controller. The controller may be configured to maintain gas saturation using an automated pH controller system comprising a water pump. The water pump may be attached to a helical vane that is housed within a pipe. The controller may be further configured to determine that there is an adequate supply of carbon dioxide when the pH rises above a threshold value. The controller may be further configured to transmit a signal configured to close a contact, wherein closing the contact activates a motor that allows carbon dioxide to flow from a carbon dioxide tank into the pipe housing the helical vane.

These and other aspects of the present disclosure will become more fully understood upon a review of the detailed description, which follows. Other aspects, features, and embodiments of the present disclosure will become apparent to those of ordinary skill in the art, upon reviewing the following description of specific, exemplary embodiments of the present disclosure in conjunction with the accompanying figures. While features of the present disclosure may be discussed relative to certain embodiments and figures below, all embodiments of the present disclosure can include one or more of the advantageous features discussed herein. In other words, while one or more embodiments may be discussed as having certain advantageous features, one or more of such features may also be used in accordance with the various embodiments of the disclosure discussed herein. In similar fashion, while exemplary embodiments may be discussed below as device, system, or method embodiments it should be understood that such exemplary embodiments can be implemented in various devices, systems, and methods.

BRIEF DESCRIPTION OF THE DRAWINGS

FIG. 1A illustrates an example of a helical vane secured in a pipe in accordance with various embodiments of the present disclosure.

FIG. 1B illustrates a first example of a portion of a helical vane in a pipe in accordance with various embodiments of the present disclosure.

FIG. 1C illustrates a second example of a portion of a helical vane in a pipe in accordance with various embodiments of the present disclosure.

FIG. 1D illustrates a third example of a portion of a helical vane in a pipe in accordance with various embodiments of the present disclosure.

FIG. 4 illustrates an example of a venturi attached upstream of the helical vane for enhanced transfer of gases into liquids in accordance with various embodiments of the present disclosure.

FIG. 6A illustrates a first example of gas injected into a helical vane in accordance with various embodiments of the present disclosure.

FIG. 6B illustrates a second example of gas injected into a helical vane in accordance with various embodiments of the present disclosure.

FIG. 6C illustrates a third example of gas injected into a helical vane in accordance with various embodiments of the present disclosure.

FIG. 6D illustrates a fourth example of gas injected into a helical vane in accordance with various embodiments of the present disclosure.

DETAILED DESCRIPTION

Figures 2A, 2B:
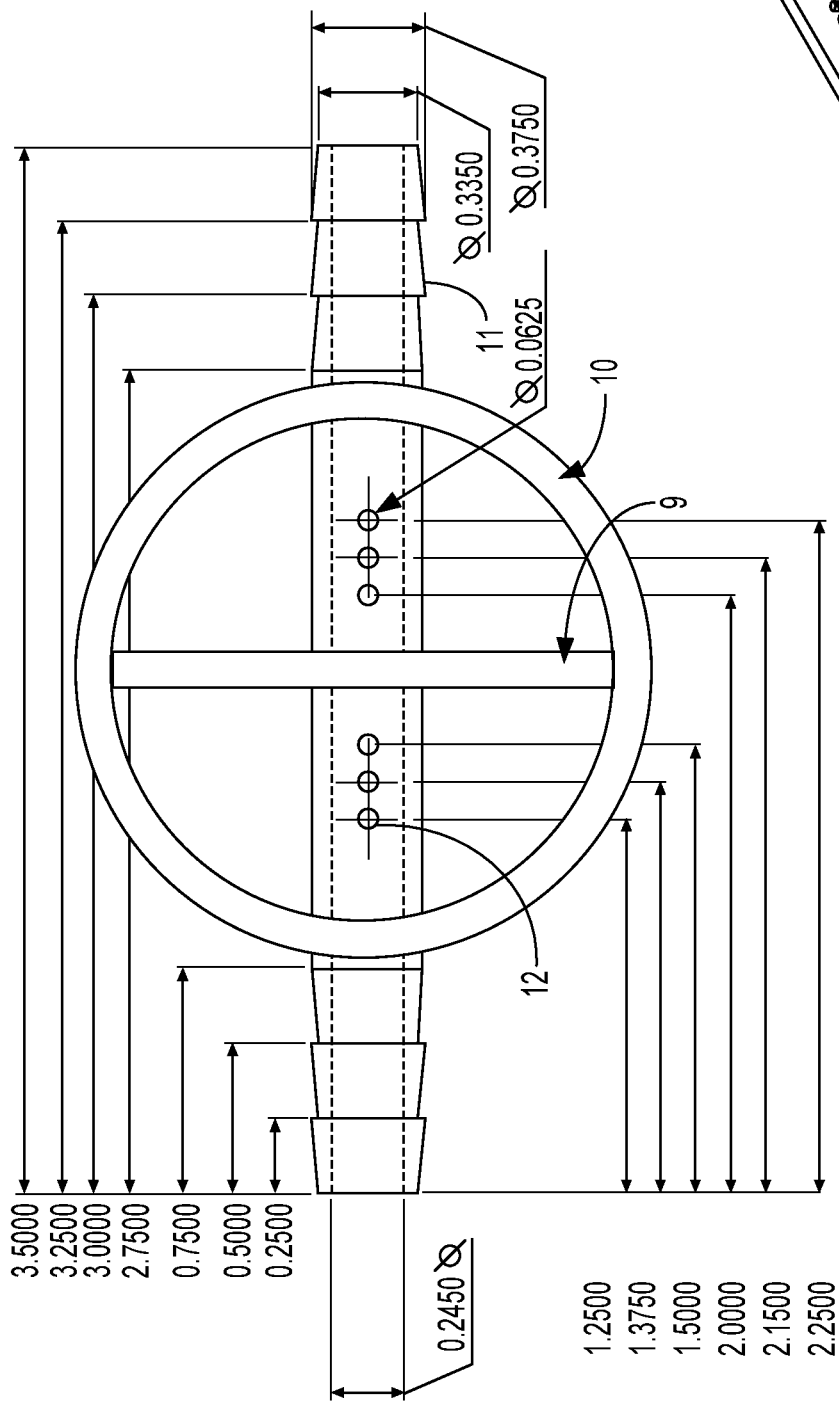
FIG. 2A illustrates a first view of an example of a hollow pin for injection of a gas in accordance with various embodiments of the present disclosure.
FIG. 2B illustrates a second view of an example of a hollow pin for injection of a gas in accordance with various embodiments of the present disclosure.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

One of ordinary skill in the art will understand that similar features and/or elements described herein may be associated with various (e.g., different) reference characters (e.g., numbers) without necessarily implying that such features and/or elements are dissimilar or different. One of ordinary skill in the art will understand that each reference character (e.g., number) shall be construed and interpreted based on the context in which it is used in each particular instance. One of ordinary skill in the art will also understand that some reference characters (e.g., numbers) may not be repeated for each and every reference to similar features and/or elements; however the omission of any reference character (e.g., number) is not necessarily intended to indicate that such features and/or elements are not similar.

FIG. 1A illustrates an example of a helical vane in a pipe. FIGS. 1B-1D illustrate various examples of a portion of a helical vane in a pipe. In particular, FIGS. 1A-1D illustrate various examples of a helical vane secured in a pipe without the need of adhesive glues. Occasions may arise where the vane made of a specific material needs to be secured in a pipe made of material incompatible for proper adhesion for dissolving different gases into various liquids. A tongue and groove attachment method will properly secure the helical vane, which may be typically exposed to the stress of pumped liquid pressurizing around the vane and through the pipe.

By manufacturing the vane with a tongue located in an upstream beginning portion of the helical vane, which fits into matching grooves in the pipe, the helical vane can be properly secured within the pipe and without the need to rely on adhesives. In part, FIGS. 1A-1D illustrate liquid flow through a pipe 3 with a vane attached 4 and passages 1, 2 on the top of the vane tongue that slides into a groove 5 of the pipe 6. Tongue and groove may be cut to size depending upon the size of the pipe and corresponding size of the vane. Liquid flows past the upstream top of the vane 8 and through the pipe 6.

FIGS. 2A, 2B, 3, and 4 show efficient injection designs that allow for efficient distribution of gases into pipes, which results in improved transfer of gases into liquids. Tests have determined that specific methods of gas injection into the pipe housing the helical vane, may be optimized for efficiency. Some designs include an air hose barb attached to the pipe that houses the vane. Such designs may include a single port for gas injection. Testing the vane concluded that sometimes in some situations injected gas competes with water flow and cannot disperse properly in pipe using a single air hose barb connection without incorporation of additional gas dispersion techniques. Injecting gas using a higher pressure (e.g., pounds per square inch (PSI)) does push gas further into the pipe chamber; however, the extra gas is wasteful, and this may be a less efficient method of transferring gas into liquid.

FIGS. 2A-2B illustrate an example of a hollow pin for injection of a gas. The pin is barbed on both ends for air hose attachments. Gas is exposed at both ends of the pin and collides in the center. Such a collision disperses gas into the pipe that houses the helical vane through the drilled holes. Such a design also allows for two different gases to be connected. The pin may include six holes drilled in the downstream-side to allow for gas to flow into pipe chamber without competing against incoming water flow. A fewer number of relatively larger holes may be used. Alternatively, a greater number of relatively smaller holes may be used. Multiple holes allow for better distribution of injected gases before the liquid moves through the vane. As illustrated in FIG. 2A, the helical vane 9 and the pipe 10 is drilled to allow for a custom steel pin 11 to be inserted. The pin 11 may have multiple holes 12 pointed downstream, which may allow for the release of gas into the upstream section of pipe housing helical vane. Illustrated in FIG. 2B is a side view 13 of the pin.

Figure 3:
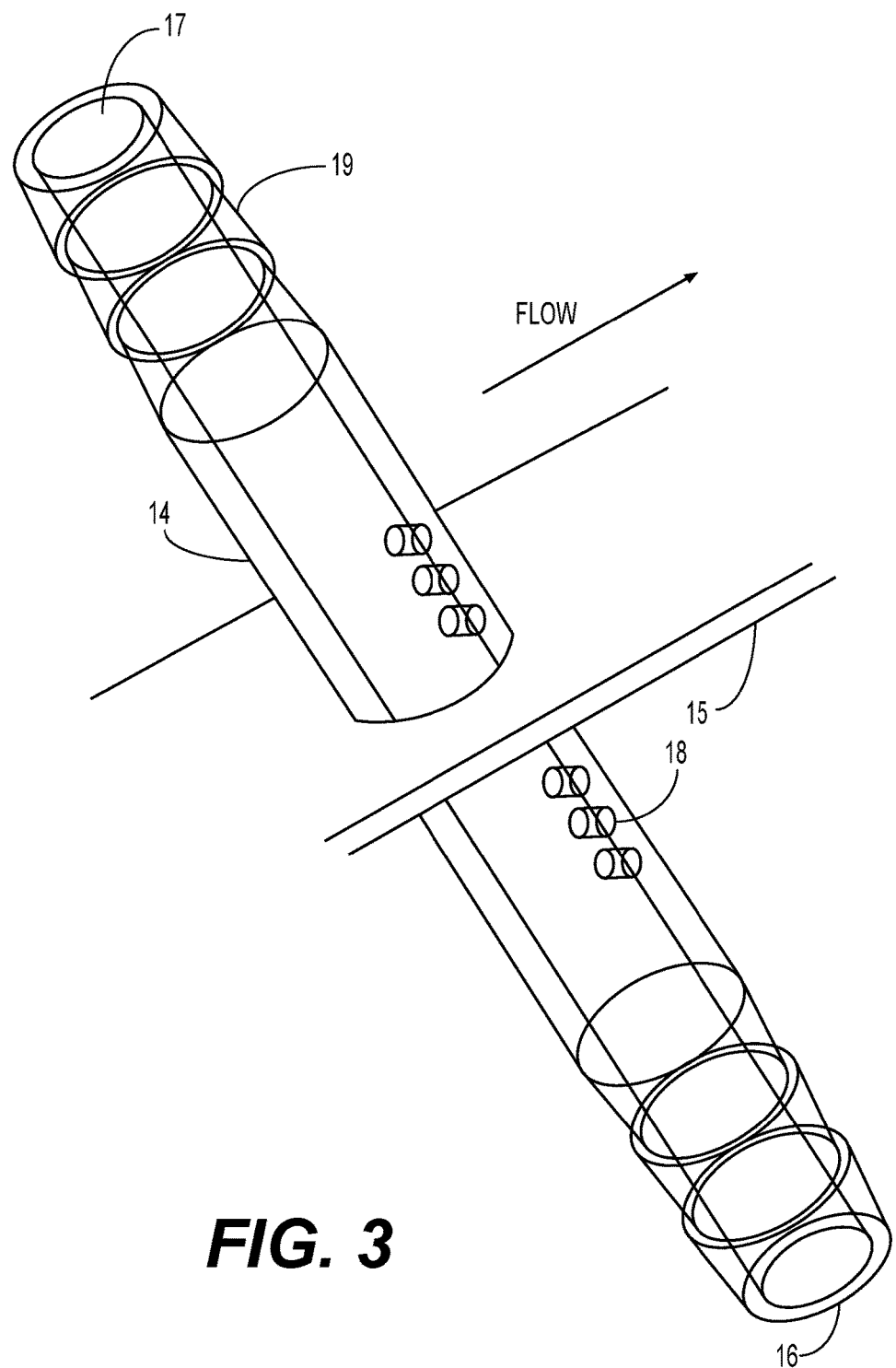
FIG. 3 illustrates an example of a steel pin positioned through the helical vane for dispersing gas in accordance with various embodiments of the present disclosure.

FIG. 3 illustrates the steel pin positioned through the vane for dispersing gas in an efficient manner. The pin 14 may be positioned through the vane 15 and one air hose may be connected to the barb 16. Another air hose may be connected to the barb 17 and injected gas or gases collide at the midsection of the pin. As a result of such a collision, gases may be ejected through the drilled holes 18, which are pointed downstream. Air hose is secured by barbs 19 on the pin.

FIG. 4 illustrates a venturi attached upstream of the helical vane for enhanced transfer of gases into liquids. A method of mixing gas and liquid may include passing liquid through a venturi to create a low pressure zone, thereby exposing a supply of gas to the low pressure zone adjacent the venture. This may allow low pressure suction to extract gas from the gas supply and expose the gas to more liquid before entering the pipe housing the helical vane.

The inside diameter of a conduit through which the liquid flows may be reduced when a venturi is connected, which creates a low pressure zone. A gas supply may be exposed to the low pressure zone and the gas from the gas supply may be allowed to enter the liquid. The gas and the liquid mixture may pass through the pipe housing the helical vane, to further reduce the size of the gas bubbles and thereby increase the surface tension of the gas bubbles mixing with the liquid, thereby enabling an enhanced efficiency of the gas transferring into the liquid.

The venturi section may decrease the diameter of the inside circumference of the venturi injector valve, thereby increasing the velocity of the liquid in the valve. A low pressure or suction area adjacent to the outlet of the gas supply hose is thereby created. As illustrated in FIG. 4, a venturi may be upstream where less flow of water can achieve high rates of gas transfer. An area 20 may include an air hose barb attached to a check valve 21, which may be connected to a venturi 22. A threaded adapter 23 may be placed over the helical vane 25 and attached to a threaded venturi 22, as illustrated in the positioning 24 of FIG. 4.

Figure 5A:
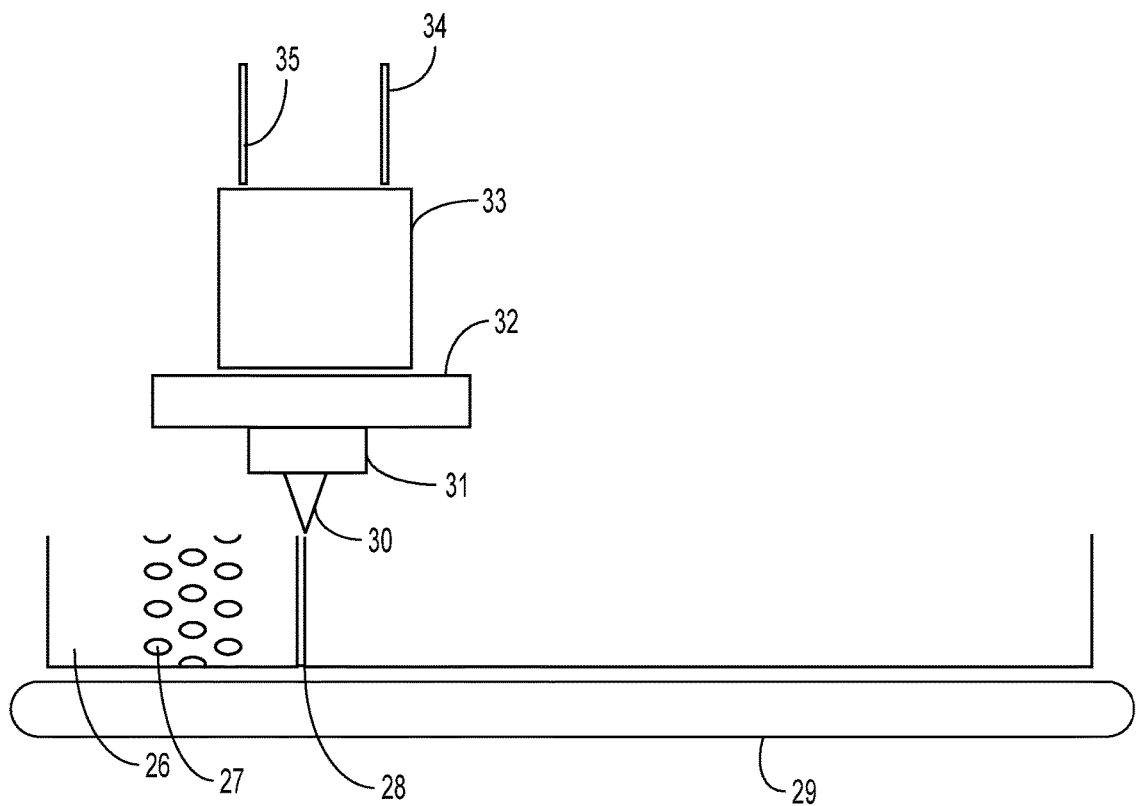
FIG. 5A illustrates an example of a process for manufacturing a helical vane in accordance with various embodiments of the present disclosure.
Figure 5B:
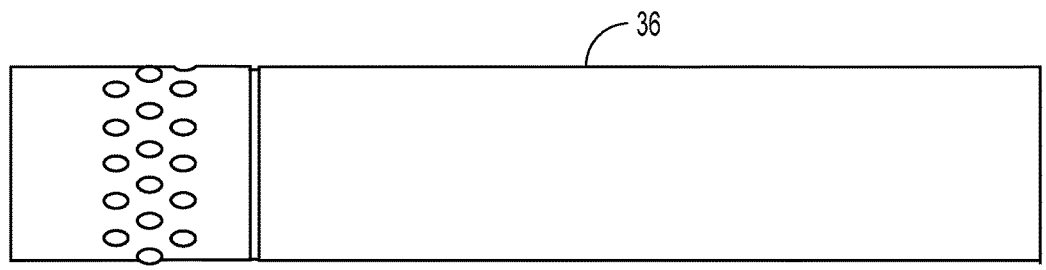
FIG. 5B illustrates an example of a manufactured helical vane in accordance with various embodiments of the present disclosure.

FIG. 5A illustrates an example of a process for manufacturing a helical vane. FIG. 5B illustrates an example of a manufactured helical vane. Some designs may use heating and bending of plastics (e.g., PVC plastics). In some embodiments of the present disclosure, three-dimensional (3D) printers may be used to manufacture (e.g., print) the helical vane as described further below. Using 3D printers, the helical vane may be manufactured (e.g., printed) to exact specifications.

In various experiments, a controlled test was performed wherein the helical vane was manufactured (e.g., printed) using PVC plastics, acrylonitrile butadiene styrene (ABS) plastics, and nylon plastics. A printed vane was then slotted into the pipe. When connected to a ½ horsepower (hp) pump and oxygen bottle, the vane and the pipe (e.g., a static aerator) oxygenated a full 40 gallon barrel of tap water at 15° C., 8 parts per million (ppm) to 35 ppm dissolved oxygen in approximately 3 minutes. Using the aforementioned process of heating and bending PVC plastics, a helical vane was produced. Once attached into a pipe, a pump, and an oxygen bottle, the vane oxygenated a 40 gallon barrel of tap water at 15° C. to 24 ppm dissolved oxygen in approximately 3 minutes. The same dissolved oxygen (DO) meter was used in both tests. It was evident that printing the helical vane using a 3D printer resulted in much higher gas to liquid transfer efficiencies due to the exactness of 3D printing compared to heating and bending plastics (e.g., PVC plastics).

Heating and bending plastic to may not be the most efficient method for manufacturing the helical vane. Injection molds may also not be most efficient method for manufacturing the helical vane due to the variable pitch of the helical vane. However, manufacturing the helical vane using a 3D printer, while much slower for production, can accommodate the gas injection needs. The helical vane and tube can be printed using nylon, PVC, and/or other compatible filament with high tensile strength to withstand the force of water flowing at high speeds.

As illustrated in FIGS. 5A-5B, the helical vane 26 is printed from the bottom up with small holes 27 left open for gas injection (see, e.g., FIGS. 6A-6B for additional details). A groove 28 around the vane tube may be made to accommodate an o-ring. The printer platen 29 may support the printed object. Plastic filament may be ejected 30 by the pre-heating of the plastic filament by the heat sink 31. A buffer heat sink 32 may keep heat away from the filament gear box 33. One or more types of filament 34, 35 spool feed into the gear box. Reference character 36 illustrates a fully printed helical vane and conduit as printed in one, single piece.

In some embodiments, the tube and vane are printed together. The pipe may fit snug over the tube and vane, which may be glued if possible for the substrates and/or alloys used. In some embodiments, nylon may be used. Nylon is believed not to be a hazard in applications where potable water is involved. Nylon is strong; however, nylon does not adhere easily to surfaces. Methods of 3D printing may include heat extrusion methods and sintering methods, among others described herein and also understood by one of ordinary skill in the art. In some embodiments, the vane may be 3D printed as a separate piece, such as the non-limiting example illustrated in FIG. 3. Subsequently, a custom stainless steel pin, such as the non-limiting example illustrated in FIGS. 2A, 2B, and 3, may be stabbed to the 3D printed vane. In some embodiments, the vane and tube may be 3D printed in one piece when a micro-hose/o-ring method is implemented, as described in further detail herein.

FIGS. 6A-6B illustrate an example of technology that disperses gas injected into a helical vane. In particular, FIGS. 6A-6B illustrate a method of injecting gas into the helical vane in an evenly distributed manner, thereby contributing to a better exchange of gas into liquid through the helical vane. A custom designed helical vane creates a low-pressure area that draws gas into the helical vane through multiple small holes. FIGS. 6A-6B show how liquid is pumped into a T-joint 38 and gas is injected through a port 39. A low pressure condition may exist as the rubber o-ring 41 may prevent gas from passing the o-ring causing gas suction through holes or alternatively small holes can be replaced by a porous membrane, into the conduit, upstream of the helical vane due to the low pressure. The helical vane 42 is illustrated with the tube as a singly-created object. An external pipe 43 may be secured over the helical vane 42 and glued at an area 38 to the T-joint.

FIG. 6C illustrates another example of gas injected into a helical vane in accordance with various embodiments of the present disclosure. FIG. 6D illustrates an exploded view of the example illustrated in FIG. 6C. A pipe portion 602 may be pushed over a porous membrane 604. The porous membrane may include various pores of various sizes without deviating from the scope of the present disclosure. The porous membrane 604 may allow gases to disperse uniformly around the fluid flow. The pipe portion 602 and the porous membrane 604 may be pushed into a reducing T portion 606. The outer wall of the pipe portion 602 may be glued to the inner wall of the reducing T portion 606. Prior to applying the glue, a clear primer may be applied and allowed to dry for a few minutes. A reducing bushing 610 may be partly inserted into an opening of the reducing T portion 606. A one-touch fitting male connector 608 may be partly inserted into an opening of the reducing bushing 610. Gases may enter through the one-touch fitting male connector 608 and the reducing busing 610, as illustrated in FIG. 6C.

A 3D printed tube 614 and a 3D printed vane 616 may be printed as a single piece (using a 3D printer). An o-ring 612 may be manually placed in a groove located near an end region of the 3D printed tube 614. That end region of the 3D printed tube 614 may be inserted or pushed into an opening of the reducing T portion 606. That end region of the 3D printed tube 614 may then be positioned to fit snugly with an inner wall of the porous membrane 614 (which is located inside of the reducing T portion 606, as described above). An outer wall portion 618 may fit tightly over the 3D printed tube 614 and the 3D printed vane 616 such that the 3D printed tube 614 and the 3D printed vane 616 will not change positions during use. An end of the outer wall portion 618 may be glued to an inner wall of the reducing T portion 606. Prior to applying the glue, a clear primer may be applied and allowed to dry for a few minutes.

With respect various embodiments described in greater detail herein, the terms pipe and tube may include various meanings without deviating from the scope of the present disclosure. For example, a pipe may refer to a tongue-and-groove, stainless steel pin method of securing a vane. A pipe can be a schedule 40 polyvinyl chloride (PVC) plastic, stainless steel, and/or any other plastic and/or metal. As another example, a tube may refer to a one-piece 3D printed item that includes a vane. A tube may be associated with a porous membrane or small-hole perforations for gas disbursement. A pipe may slide over a printed tube housing a vane, wherein an o-ring manually positioned on the groove of the tube comes in contact with an inner surface of the pipe. Thus at least two versions are disclosed: one with a pipe that forms an inner conduit in which the vane resides; another with a tube in which the vane is integral with, and forms, an inner conduit immediately surrounding the vane, which tube itself may be surrounded by a pipe, for example, for strength and/or certification purposes. In some embodiments, the integral printed tube itself can be the sole conduit, but for cost and various other reasons it may be desirable to surround such a tube with a surrounding pipe. Accordingly, examples of conduits include pipes and tubes, as well as pipe and tube combinations. The term "pipe" as used herein is generic also to both a conduit and/or a tube, and, thus, the term "pipe" includes, e.g., a PVC and/or other conventional pipe, a modified or customized pipe of any material or materials, any specialized pipe, and further refers to any structure (e.g. a tube) immediately surrounding the vane to form a flow path related to the vane.

Figure 7:
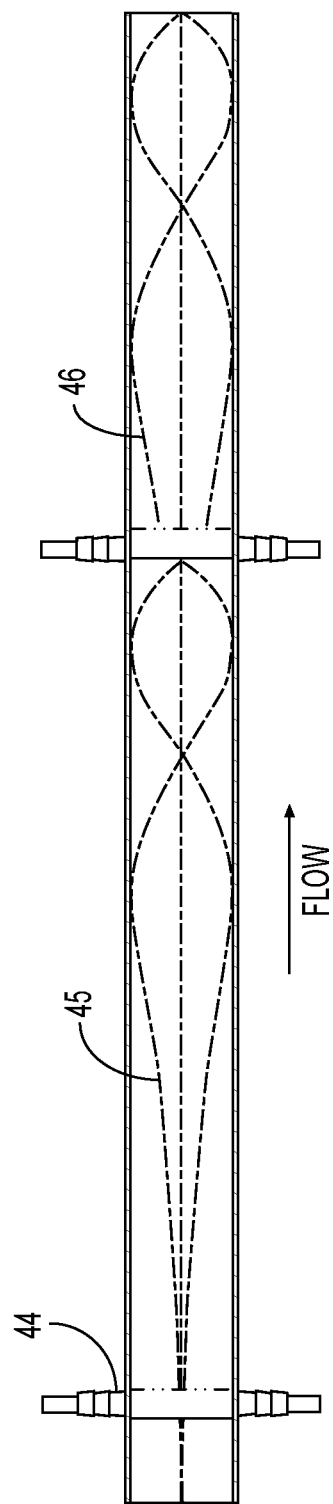
FIG. 7 illustrates an example of two helical vanes in a single pipe in accordance with various embodiments of the present disclosure.

FIG. 7 illustrates an example of one vane with another helical vane of less length in a single pipe. The example illustrated in FIG. 7 may enable higher gas saturation with more gas injected in real time, while the increased pressure increases the gas transferred to the liquid. Some existing designs may inject gas into the pipe using one hose barb on a single side of the helical vane. However with the added, shortened second vane inline positioned downstream of first vane, and with additional gas injection ports, the example illustrated in FIG. 7 provides the possibility that more gas could be transferred efficiently into the same flow of liquid using two vanes inline as compared to a single vane, without the need for recirculation. While this method may lessen water flow, there may exist occasions where less liquid volume and more dissolved gas may be needed.

The portion 44 illustrates a set of two steel pins where gas may enter the vane (see, e.g., FIGS. 2-3 for additional details), and the gas may be exposed to the liquid within the vane 45 chamber. An additional helical vane 46 with 30% of the top-end removed may be secured within the pipe to enable an increased dissolving of the gas into the liquid.

Figure 8:
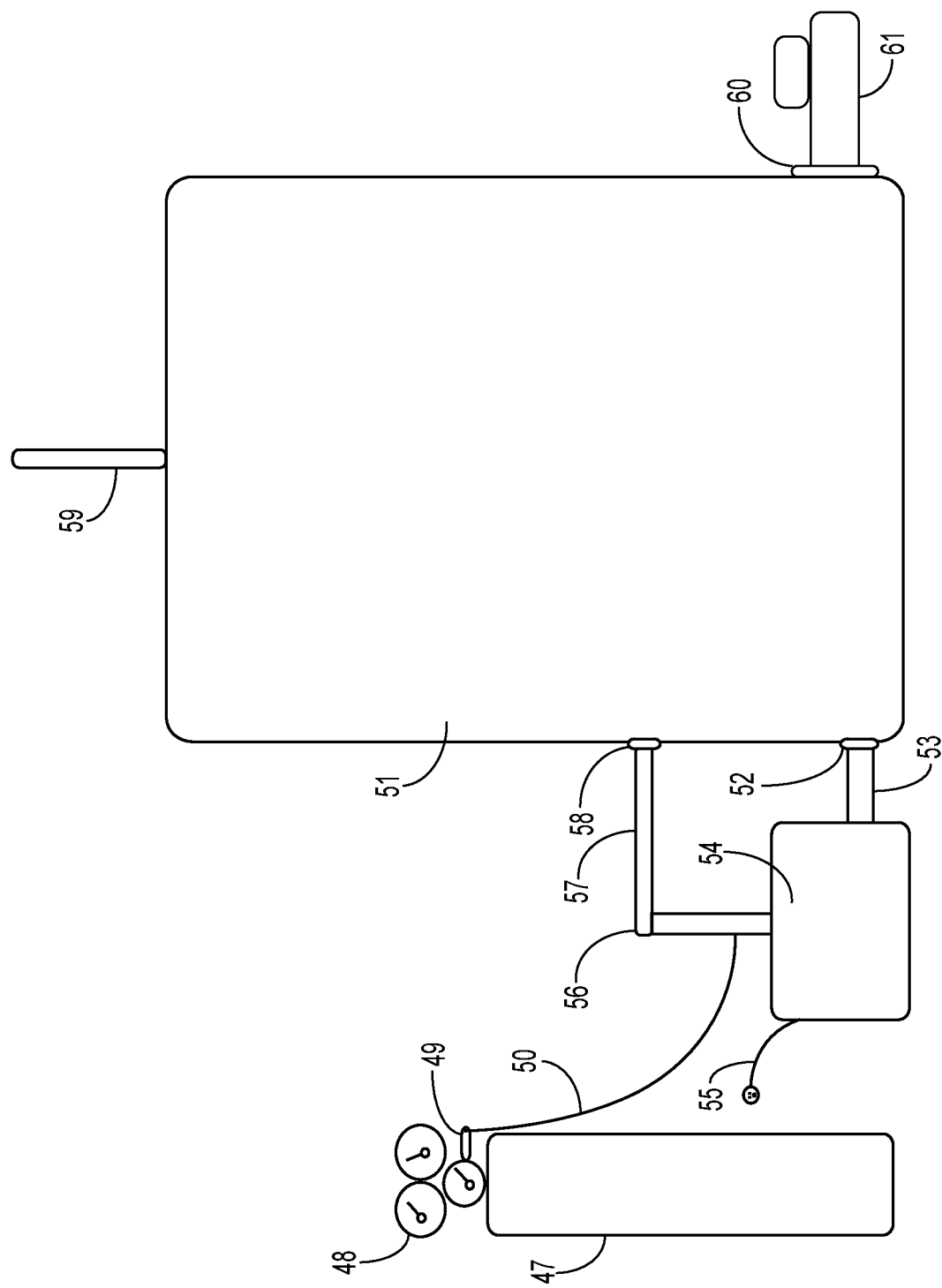
FIG. 8 illustrates an example an apparatus that recirculates treated water in accordance with various embodiments of the present disclosure.

FIG. 8 illustrates an example an apparatus that recirculates treated liquid to increase dissolved gas levels. The helical vane may imperfectly transfer a limited amount of gas into liquid. There may exist requirements wherein higher dissolved oxygen levels or other gases in liquid are required. In some cases, diffusers are used that diffuse gas into water until the desired level of gas saturation is achieved, and such levels may be substantially higher than those provided for in existing designs. For the helical vane technology to contend in an industry that deploys aerators, diffusers or other methods of gas transfer, higher dissolved gas levels may need to be achieved than the vane presently attains. As illustrated in FIG. 8, a gas 47 may pass through a regulator 48, which may control the outflow of gas. The gas may travel into a helical vane pump assembly (see, e.g., FIG. 12), where the gas is mixed into a liquid. A liquid residing in a reservoir 51 may be pumped through a bulkhead 52 and through a pipe 53 into a pump vane assembly (see, e.g., FIG. 12). In the pump vane assembly, the injected gas 50 may encounter flowing liquid. The gas is transferred to the liquid during such a process, and the treated liquid may flow through a pipe elbow 56, through a pipe 57, through a bulkhead 58, and ultimately back into the reservoir 51 containing liquid. In the reservoir 51, additional recirculation may occur in order to increase gas levels in the liquid. A pipe 59 may be used to fill liquid in the reservoir 51. To release the treated liquid, a ball valve 61 may be attached to the bulkhead 60. The ball valve 61 may be opened to drain the reservoir 51 of the treated liquid.

In some embodiments, the gas may be oxygen and the liquid may be water. A pump with an attached vane may dissolve up to 22 ppm of oxygen in the water. In some embodiments, oxygen gas levels in the water may attain levels as high as 60 ppm of oxygen when treated water recirculates. In some embodiments, the amount of gas transfer may be increased by up to 300% (or more).

Figure 9:
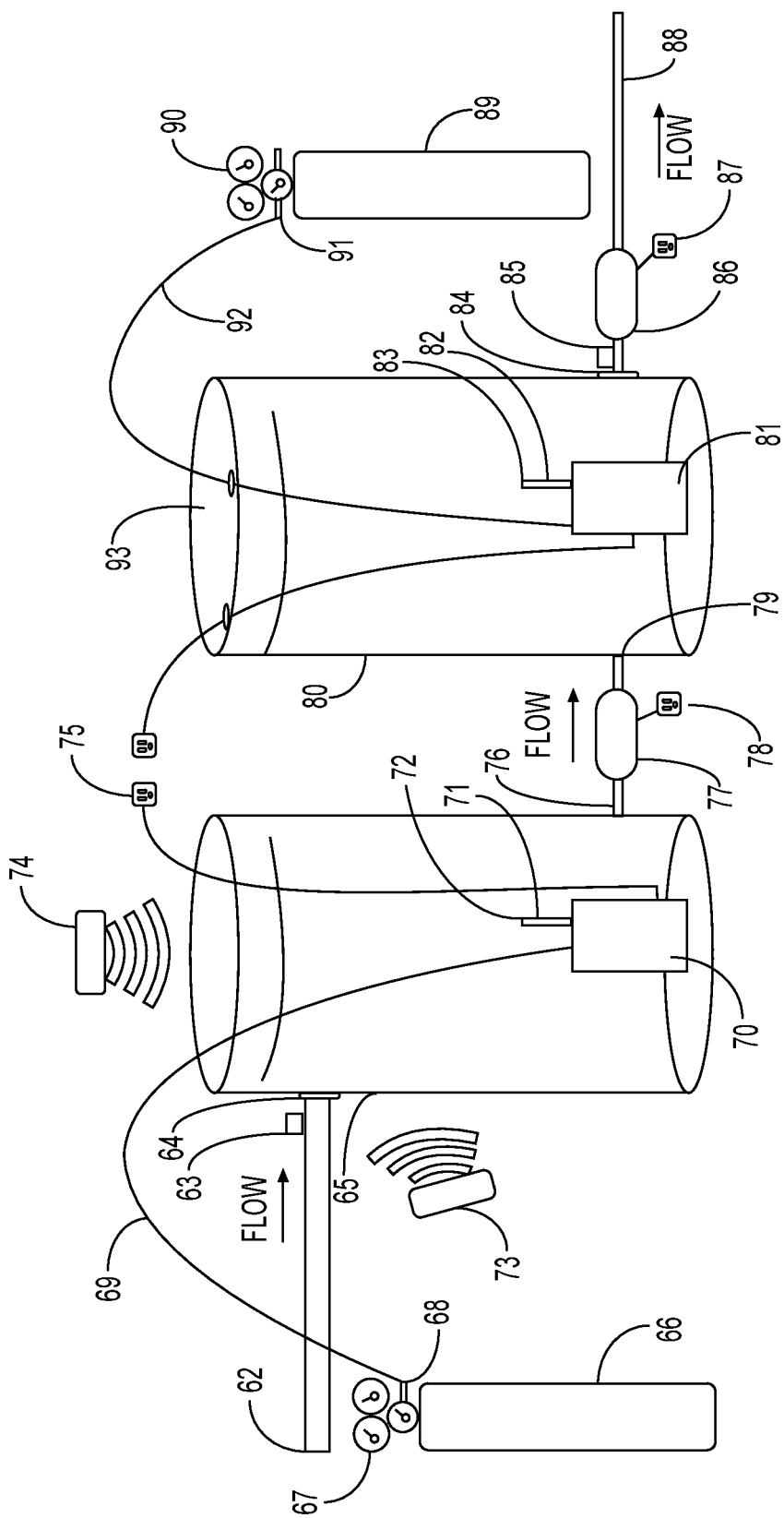
FIG. 9 illustrates an example of a bio-reactor in accordance with various embodiments of the present disclosure.

FIG. 9 illustrates an example of a bio-reactor. In some embodiments, the bio-reactor may be used by farmers and others for treating algae, converting water to an organic plant food, and various other suitable applications. Algae may bloom in lakes and ponds and may be considered a health hazard to farmers, boaters, swimmers and even to drinking water. Aerators, and/or diffusers are often deployed to reduce the impact of algae blooms. However, due to the large bubble size produced by these bubble systems, the oxygen may rapidly rise to the surface, often making these systems ineffective in reducing algae blooms. In addition, such systems are static in nature and may apply predominantly to a localized area. In some circumstances, destratification may result from these systems Destratification may occur when cooler water is pumped from the bottom, or their bubbles push cooler water from the bottom of a lake. This may result in the exchanging of cool water from lower levels with warm water from higher levels.

Such results may greatly impact the types of aquatic life that survive predominantly at specific temperatures. Further, the aeration may also disturb the bottom sediment, which may mix into all water depths, release stored nutrients, and increase oxygen demand. Farms, golf courses, ponds, lakes and aquifers have experienced many algal blooms in recent times due to warmer water as is believed to be caused by climate change (e.g., global warming) and nutrient buildup from fertilizer runoff. Such conditions may create an eyesore for golfers, a hazard to farms (as the algae cannot be collected or removed in a cost effective manner), thereby leaving agricultural workers no choice but to purchase and use government supplied water.

Algae may be harvested in controlled environments and used for feedstock, soil amending and fuel. However, harvesting algae may be an expensive operation that typically requires expensive centrifuges and machinery. Compost tea refers to a method wherein gardeners place a bag of soil bacteria in water that has nutrients added and aerated for 24 hours or more. Aerobic bacteria, such as rhizobacteria, proliferate in the oxygen-rich and nutrient-rich environment. The solution is then fed to plants for enhance health and growth.

The helical vane may be used in conjunction with a custom bio-reactor to collect, grow, control, and/or terminate algae and/or bacteria in water. The algae and/or bacteria can then be applied to plants as a soil conditioner, which may be known as compost tea. Such a process may turn a liability (algae in ponds) into an asset. Algae can be considered a super-food when harvested in controlled environments. The growth rate of algae can be enhanced with the addition of carbon dioxide and light. By oxygenating algae-infested water to levels over 24 ppm DO, sustained for a number of hours, and blocking any light penetration, the algae may die and sink to the bottom. Aerobic bacteria and aerobic-loving fungi can be purchased from various suppliers, and the same can be added to the oxygenated water, or even bacteria from soil can be added, which may also contain beneficial fungi. The aerobic bacteria or fungi may proliferate throughout the water, thereby consuming the nutrient-rich dead algae as food stock. As such, the process may produce compost tea from algae, which may be a perfect soil conditioner for farms, golf courses, and various other applications.

FIG. 9 illustrates an example of a method for converting algae-infested water into an organic plant nutrient solution that can be applied to plants and/or vegetable gardens. Water from a pond or an algae water source may be pumped through a pipe 62 via an open ball valve 63, through a bulkhead 64, and into a water tank 65. Carbon dioxide may be stored in a steel tank 66 and, when released by a regulator 67, the gas may flow out of a brass barb 68 through an air hose 69 and into a submersible pump/vane assembly 70. Carbon dioxide may be exposed to water in a helical vane 71 and treated algae water ejects from an end of a vane 72. Carbon dioxide may be added to increase the density of the algae in water. For example, if the algal water contains high concentrations of nitrogen and/or phosphorus, additional light sources 73, 74 may be provided to increase the rate of algae growth. As the rate of algae growth increases, the rate of the consumption of nitrogen and phosphorus may increase as well.

Various pumps 70, 81 may plug into various power sources 75. When algae treatment is complete, water may flow into a pipe 76 and a transfer pump 77 may be manually activated by connecting power 78 to an electric outlet. Treated water may be pumped through a pipe 79 and fill up a black tank. The black tank may have an exterior layer 80 having a dark-colored covering and/or paint in order to block sunlight from reaching the algal water. A second submersible pump 81 may be activated by connecting a power cord to a power source 75. Water may be pumped through a vane exposing algal water to the injected oxygen, which dissolves into the algal water by passing through a helical vane 82 and ejecting into a body of water at an end region 83 of the helical vane 82. In some embodiments, aerobic bacteria may be added. The aerobic bacteria may consume the dead algae as a feed stock.

When oxygen levels surpass 24 ppm DO, algae may begin to die. After hours of treatment, the oxygen bottle 89 with the regulator 90 may be closed, thereby stopping oxygen from flowing through hose barb 91 and, consequently, flowing through an air hose 92 and into a pump vane assembly 81. A ball valve 85 may be opened to allow the flow of oxygenated water through a bulkhead 84 and into a second transfer pump 86. The transfer pump 86 may be manually activated by plugging it into a power source 87. The oxygenated water may flow through a pipe 88 and into a field or a tanker truck. A non-pressurized lid on a black tank may be used to reduce the light entering the tank.

Figure 10A:
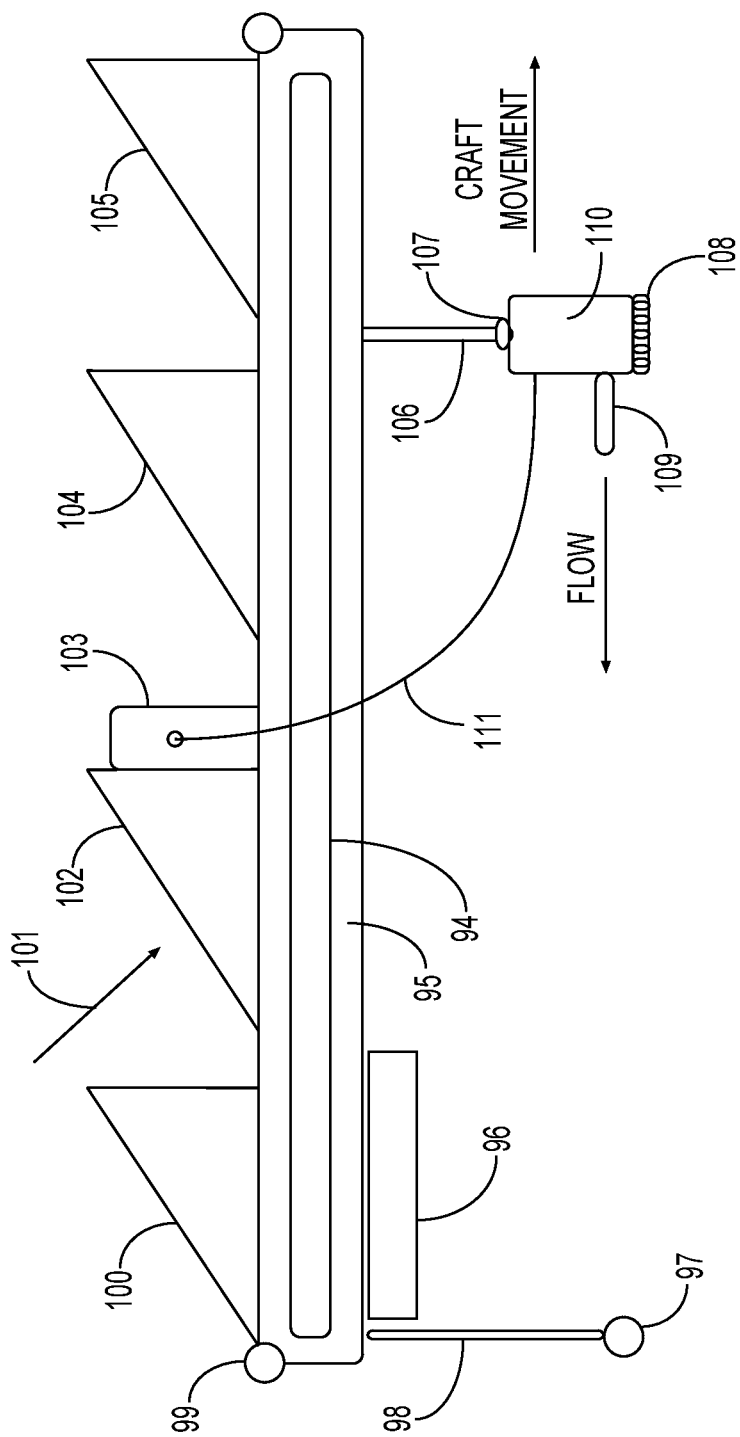
FIG. 10A illustrates a first view of an example marine craft in accordance with various embodiments of the present disclosure.
Figure 10B:
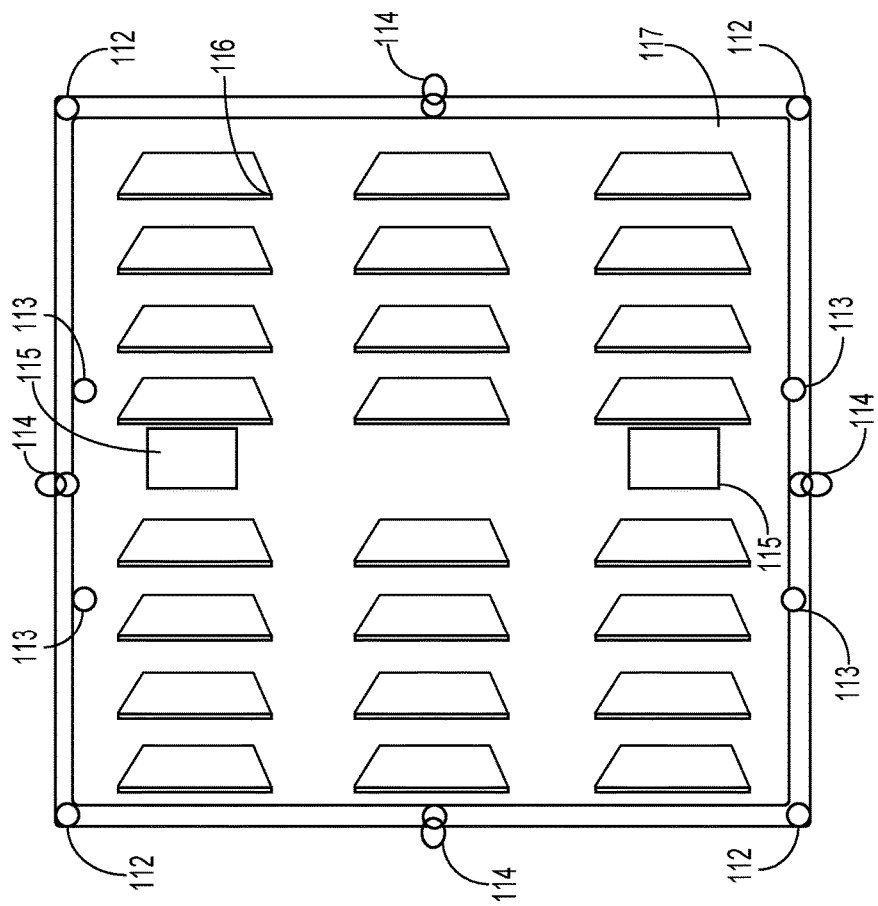
FIG. 10B illustrates a second view of the example marine craft in accordance with various embodiments of the present disclosure.
Figure 10C:
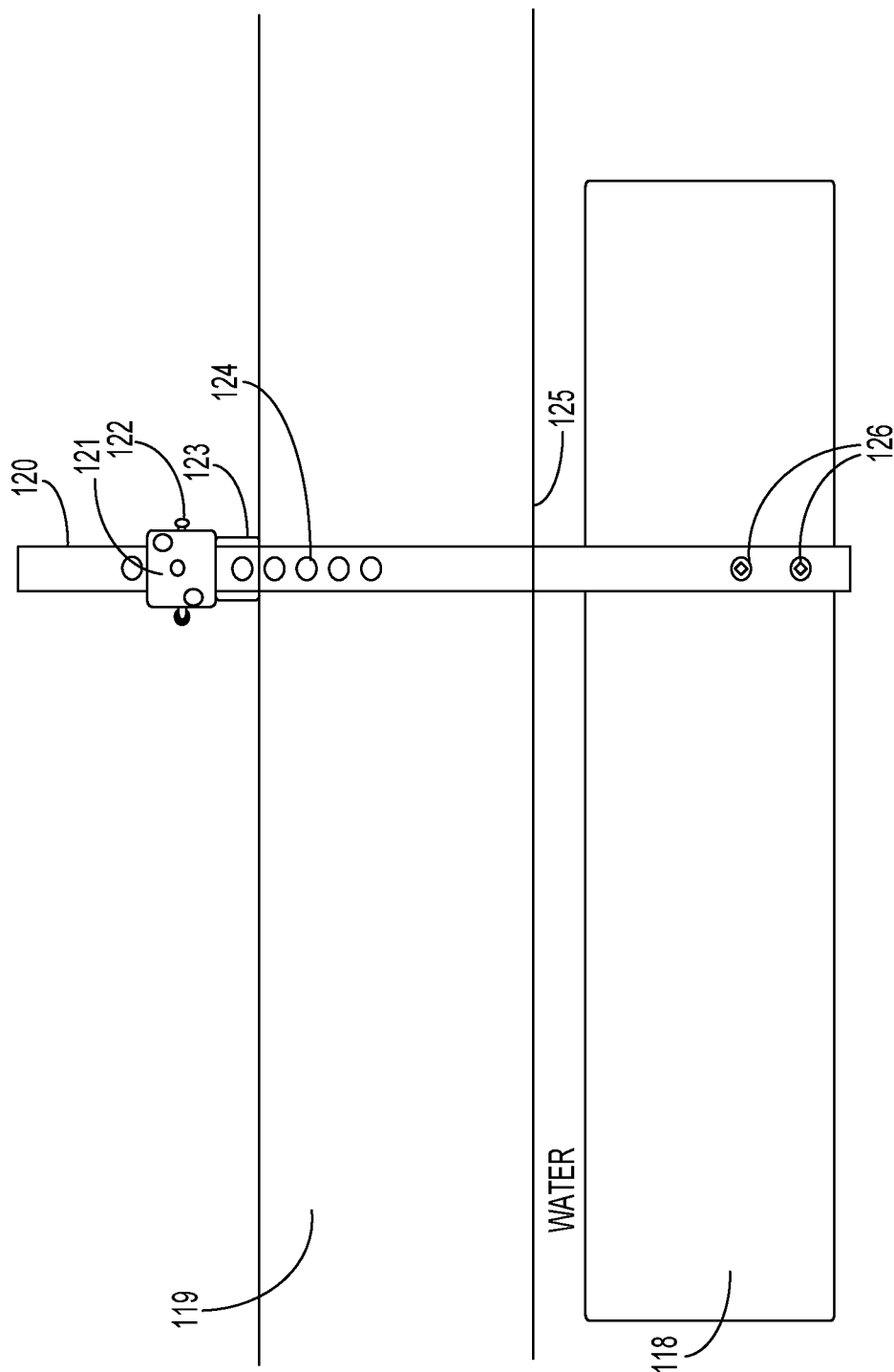
FIG. 10C illustrates a third view of the example marine craft in accordance with various embodiments of the present disclosure.

FIGS. 10A-10C illustrate examples of a marine craft. The marine craft may have various solar arrays that provide a power source for power pumps and oxygen concentrators, which may be used to push water through a helical vane and inject various gases, such as oxygen that can be supplied on demand by oxygen concentrators. The helical spin of discharging pumped water may provide jet propulsion attributes that can be used to maneuver a marine craft. The marine craft may maintain position in a manner that captures sunlight from the sun.

Many fresh water sources in North America have a relatively high iron content. This iron content, under aerobic conditions, may help sequester phosphorus buildup in lake sediment, which may have been caused by farm runoff, septic failings, and/or sewage treatment. Recently lakes have become warmer in temperature than before, perhaps due to climate change (e.g., global warming). Warmer water is more hospitable for algal blooms. Also, warmer water expands gases pressurized in lake water, thereby releasing some of the oxygen from the lake into the atmosphere. Further, lower-oxygenated water cannot react with iron in aerobic situations, and stored phosphorus is released from sediment into the water. Decades of phosphorus buildup may be become food for algae. Once a bloom occurs, the oxygen in fresh water may become even more depleted as a result of the decomposing algae, and the dissolved oxygen levels may drop even further, causing the release of more phosphorus.

The addition of iron may help sequester phosphorus in the water treated with dissolved oxygen. In some circumstances, where the sediment ratio of iron to phosphorous has declined due to pyrite formation, adding iron (if needed), in combination with oxygenation, may be an effective treatment combination.

Some processes may exist for killing algae using chemicals, ultraviolet (UV) radiation, copper and other metals. However, such processes may be harmful to aquatic life or too costly to implement in a large scale. Aerators help raise dissolved oxygen content slightly. However, such aerators are built to stay positioned in one area. Removing algae from lakes is not cost efficient. Further, typical sedimentation techniques used in sewage treatment (e.g., gravity-settling clarifiers) may not work with many algae species because they may be buoyant. It is believed that controlling or sequestering phosphorus content in lake water is more feasible for controlling or preventing algal blooms than aeration processes currently used today.

In some embodiments, a floating solar array (e.g., a barge, floating dock, or other suitable watercraft) may be used to power a magnetic drive submersible or inline pumps with the helical vane(s) attached to pumps. By re-circulating dissolved oxygen in lake, river, pond or saltwater, phosphorus release can be lessened, and algae growth can be slowed and/or halted. High levels of dissolved oxygen gained in the process enables the naturally occurring or supplemented aerobic bacteria to feed on the dead algae. The solar array provides power to the pumps and oxygen concentrators during daylight hours. By not attaching a pipe to the outflow end of the vane in the pipe, the oxygenated water may be discharged directly from the vane into the water, thereby creating propulsion due to the helical spin that discharges water directly into the lake. Such propulsion can be used to turn or move the craft to track the sun for greater solar capture or other navigational needs. Similar to a marine propeller or hydro-jet, power may be transmitted by converting rotational motion into thrust. A pressure difference is produced between the forward and rear surfaces of the airfoil-shaped blade.

Testing has shown liquid outflow from helical vane may be similar in principle. Water may increase speed as it moves through the vane, and water may exit at a faster speed than entering the vane. Although the propulsion is not significant enough to power a traditional motorboat, it is enough to move a floating craft with solar panels in the direction of the sun for maximum exposure. The 3 foot by 5 foot solar panels may weigh approximately 45 pounds each and may convert 250 Watts per panel. Four keels may be connected and manually positioned to the steer craft under pump propulsion. Each keel (which may be made of metal, plastic, carbon fiber, and/or fiberglass) is attached to a pole with pre-drilled holes above water level. A ring pin may be fitted to secure a keel angle and a keel depth manually, as needed. Keels can be turned up to 90° to slow movement of the craft. Lead weights located below the surface at each corner of the craft may control craft pitch and yaw caused by wind and/or wave forces. Stainless steel rings may be mounted on each corner of craft and center mid section. The stainless steel rings may enable quick deployment when connecting to another craft or repositioning the solar craft quickly (e.g., for anchorage). The floating craft may be built in a modular fashion, which may allow for the connection of the craft to other crafts for larger treatment needs. For example, larger crafts may be needed for oxygenating larger lakes, such as portions of Lake Erie (located in the United States).

Pitch and yaw may be minimized due to the added weight positioned deep below the craft. Manually shifting one or more keels to an obstructive position can slow craft propulsion as needed. A speed of 0.05 km/hr (50 meters/hour) or slower may be desirable for heavy algae blooms. Possibly slower speeds may be needed for craft stability in heavy winds. For additional craft propulsion, an electric powered outboard engine could be used to propel the craft. The craft may utilize a lithium battery that may be recharged using land-based electricity and/or utilizing added/dedicated solar panels on board the craft.

FIG. 10A illustrates an example of a floating platform 95. The floating platform 95 may be built from modular floating blocks sourced various suppliers and/or retailers. The floating platform 95 may also include a PVC plastic bumper 94, which may be attached to an outer perimeter. One of four keels 96 may be manually positioned for craft navigation. A lead ball 97 may help reduce pitch and yaw. A steel pole 98 may connect the lead ball 97 to the craft. One of four steel rings 99 may connect the solar craft to other water crafts or anchors. One of twenty-four solar panels 100, 102, 104, 105 may be provided. Each solar panel 100, 102, 104, 105 may receive sunlight at a best angle 101 for sunlight capture. An oxygen concentrator 103 may supply approximately 93% oxygen to a submerged pump 110 at a flow of 51 pm. A steel bar 106 may secure a pump 110 to the craft 95. A steel weld 107 may allow for customized security of the pump to the craft 95. A water inflow 108 may be included. A helical vane 109 may be used for dissolving oxygen in fresh or salt water. One of four ¾ hp submersible magnetic drive pumps 110 may be included. An air hose 109 may also be provided for transporting oxygen from concentrator to pump which ports to helical vane.

FIG. 10B illustrates an example of a top view of the solar craft, which includes one of four keels 112, one of four steel poles 113 for submersible pumps, is one of four steel rings 114 to secure the craft to other crafts or anchors, two oxygen concentrators 115 that may supply oxygen to magnetic drive pumps, each concentrator producing 12 1 pm oxygen, 61 pm per pump, one of twenty four solar panels 116, and a top deck 117 of the floating craft.

FIG. 10C illustrates an example of a side view cut-away of a section of the craft that depicts the manual set keel 118, which includes a flotation section 119 of the craft, and a steel pole 120 with pre-drilled holes for height adjustment. A collar 121 with pre-drilled holes may be attached using a ring pin or cotter pin 122 to secure a particular height and/or a particular angle. A coupling 123 may be welded to the craft and the steel collar. Several pre-drilled holes 124 may allow for manual raising of the steel pole to raise keel to a particular height. Steel holes drilled in angular pattern may enable the manual turn of keel setting for pre-set directional control. A bottom 125 of the float is in contact with water, and the keel may be secured to the steel pole with various bolts 126.

There are many applications for a solar powered craft which oxygenates fresh or saltwater. Such applications include algae treatment, supplying additional dissolved oxygen for fish under stress due to hypoxic conditions, and addition of dissolved oxygen to waste treatment ponds. With solar-generated power, land-based electric power supplies or gas-driven generators may not be needed as much as would be needed otherwise. Combined with continuous oxygen supplied by concentrators during daylight hours, the craft can be anchored for unmonitored operation. The use of magnetic drive pumps are preferred because they use fifty percent less energy, oil-less, are corrosion resistant to oxygenated water, and are submersible. Some embodiments may include two oxygen concentrators and four magnetic drive pumps per craft. The craft may be powered by a solar array that supplies 6,000 Watts of electricity. Each concentrator may draw 900 Watts, and each magnetic pump may draw 600 Watts. Each craft may oxygenate 300 gallons per minute (gpm) at approximately 18 ppm DO and use 4,200 Watts and with the craft moving at slow speed, will recirculate pre treated water, thereby increasing oxygen levels considerably higher than 18 ppm DO.

Figure 11:
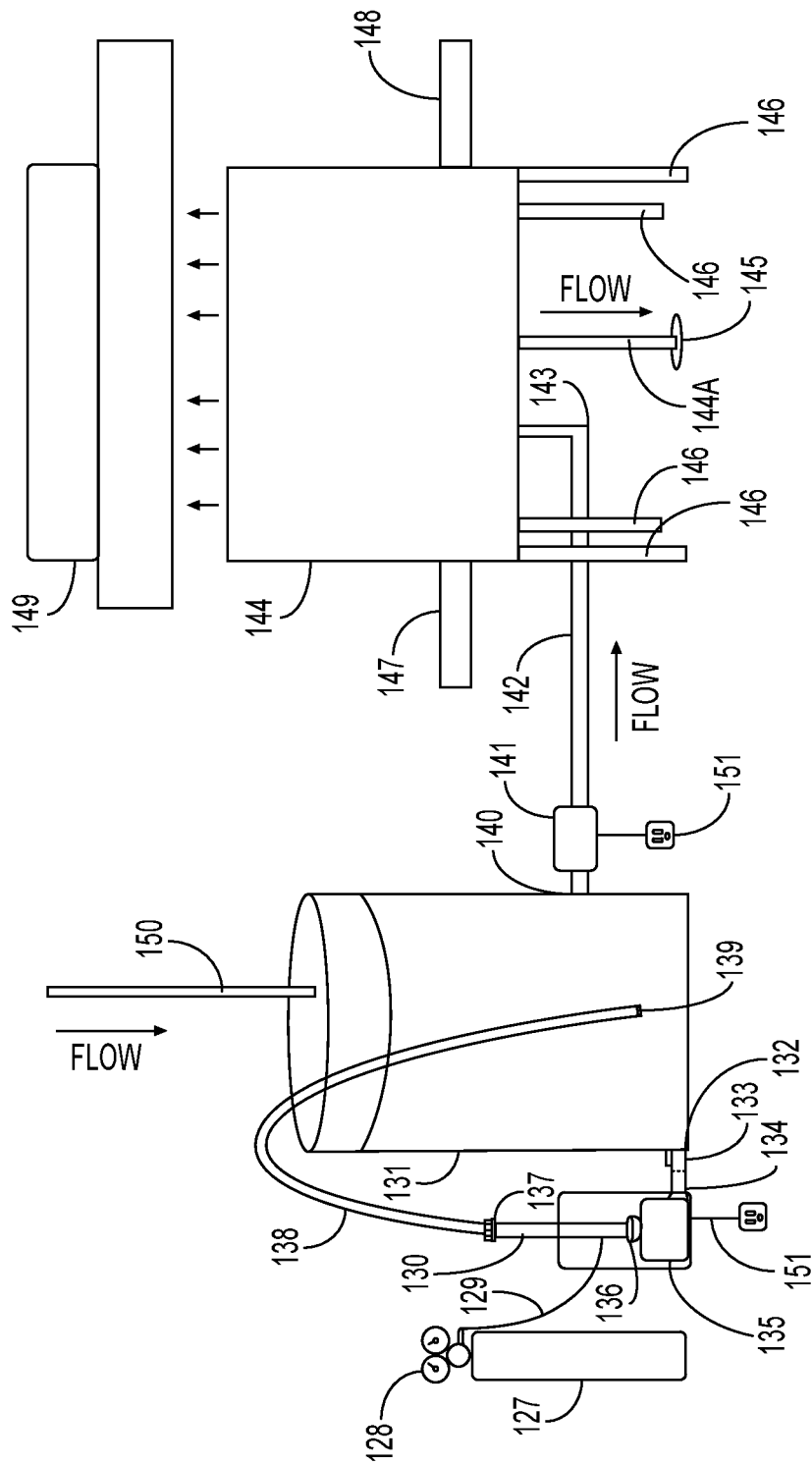
FIG. 11 illustrates an example of a dishwasher system in accordance with various embodiments of the present disclosure.

FIG. 11 illustrates an example of a dishwasher system. In some embodiments, the dishwasher system may use dissolved carbon dioxide instead of detergents for cleaning dishes, tableware, glassware and flatware. Some existing designs of dishwashers rely on heated water, detergents, and various rinsing agents for proper sanitation of dishes, tableware, and flatware. The detergents and various rinsing agents may be costly to purchase and detrimental to the local ecosystem and/or sewage treatment plants when discharged into drains.

For various embodiments of the present disclosure, an experiment was performed at a restaurant. A helical vane was attached to a ¾ hp centrifugal pump with a connection to a water reservoir. Water was treated for 15 minutes to boost carbon dioxide levels in water to 2000 ppm or greater. An on-demand transfer pump connected the carbon dioxide treated water to a dishwasher to match city water pressure of 50 pounds per square inch (psi). The on-demand pump may then be controlled by the dishwasher and activated when a pressure drop occurs. A pressure drop may occur when the water intake line of the dishwasher is opened in order to fill the dishwasher with a proper amount of water. The dishwasher used in such an experiment was similar to various commercial and/or residential dishwashers that have integrated water heaters calibrated to achieve specific temperatures for proper sanitation. In such an experiment, the dishwasher raised the incoming water temperature of 78° Fahrenheit (F) to 179° F. This increase in temperature activated the wash cycle using dissolved carbon dioxide water in place of tap water and detergents. Approximately 2 gallons of carbon dioxide treated water was used during the entire process. After the wash and rinse cycles were completed, the washed dishes and tableware were inspected for cleanliness. It was determined that the washed items were visually cleaner, shinier, and without water spots compared to items washed items using detergents and various rinsing agents. Some dishwashers may require an on-demand hot water booster to raise temperatures to 130° F. before entering the dishwasher booster pump.

Hard water issues are relieved by the low pH of the dissolved carbon dioxide in water. For example in the experiment described above, the restaurant tap water had a pH of 7.5 before treatment and, after treatment, the pH had dropped to 4.5. Calcium- and lime-scale may buildup may be typical with appliances exposed to hard water, and may prove untypical when high amounts of co2 is dissolved in water. The low pH of carbon dioxide water dissolves grease from surfaces and also dissolves the salts found in high pH water. In the foregoing example, it was observed that the wash result indicated few to no water spots or stains on the washed dishes and glassware.

The carbon dioxide gas is the same type as those used for carbonated beverages. The carbon dioxide is captured at coal power plants and others to be reused. A significant number of lakes and rivers globally are under stress from algal blooms. An example of such a lake is Lake Erie, on which millions of people depend for clean water. Accordingly, a need exists to limit the amount of phosphorus entering local watersheds in order to discourage future algal blooms. Various studies indicate that there are over 600,000 restaurants in the United States. Various studies also indicate that restaurants may spend as much as $500 per month (or more) on detergents and sanitizers. These figures suggest that such restaurants may spend an estimate of $300 million per month (or more) for detergent costs. The impact on sewage treatment facilities and damage to local streams and lakes caused by detergents is also significant. An estimate of the monthly cost of carbon dioxide for an average restaurant using a dishwashing system of the present disclosure may be approximately $50 per month and will have minimal, if any, negative impacts on local watersheds (because the carbon dioxide in water is released back into the air as hot temperatures in the dishwasher system expand the gas).

Compressed carbon dioxide 127 located in a tank or bottle may be positioned near or far from the system in accordance with various embodiments of the present disclosure. A regulator 128 may control the gas flow and pressure that flows through a connected air hose 129 and into a helical vane 130 in order to expose the gas to the water contained in a tank 131. Water may flow through a bulkhead 132, through an opened ball valve 133, through a pipe 134, and through an intake port of a pump 135, where carbon dioxide gas is exposed to the water and mixed. A first coupling 136 may connect the helical vane 133 to a pump 135. A second coupling 137 may connect an outflow end of the helical vane 133 to a flexible hose 138, which may discharge treated water 139 back into the tank 131.

The system may recirculate treated water for several minutes in order to achieve a 2000+ mg/l content of carbon dioxide in water. Subsequently, the system may be turned off by unplugging the pump 135 and closing the regulator 128. Treated water begins to flow out of the tank 131 and through a pipe 140 when the on demand transfer pump 141 is activated by a pressure drop. A pressure drop may be caused by the dishwasher intake valve opening to introduce water. Water flows through another pipe 142, through an elbow 143, and up into a dishwasher 144, where carbon dioxide water is heated to 179° F. When the washing cycle is complete, the dishwasher 144 may release dirty water down a pipe 144A and into a drain 145. Four legs 146 may stabilize the dishwasher. The objects to be sanitized may be placed on a preloading arm 147 and moved to unloading arm 148 after washing is complete. An overhead vent 149 may capture steam and remove it. New tap water may flow through a pipe 150 when refilling is required.

A typical dishwasher may use two gallons of water per treatment, and each treatment may consume ten minutes to heat, wash, and unload, which equates to six wash cycles per hour. Using a 100-gallon tank of treated carbon dioxide water, enough supply is provided for eight hours of continuous operation. (E.g., six washes per hour=12 gallons/hour=96 gallons per eight hours. Refilling an empty tank requires eight minutes. Treating 100 gallons of tap water with carbon dioxide may require 15 minutes, and such a quantity may be enough for 8 more hours of continuous use. In addition, a smaller water tank may be used when the system is connected to a custom gas saturation control system.

Figure 12:
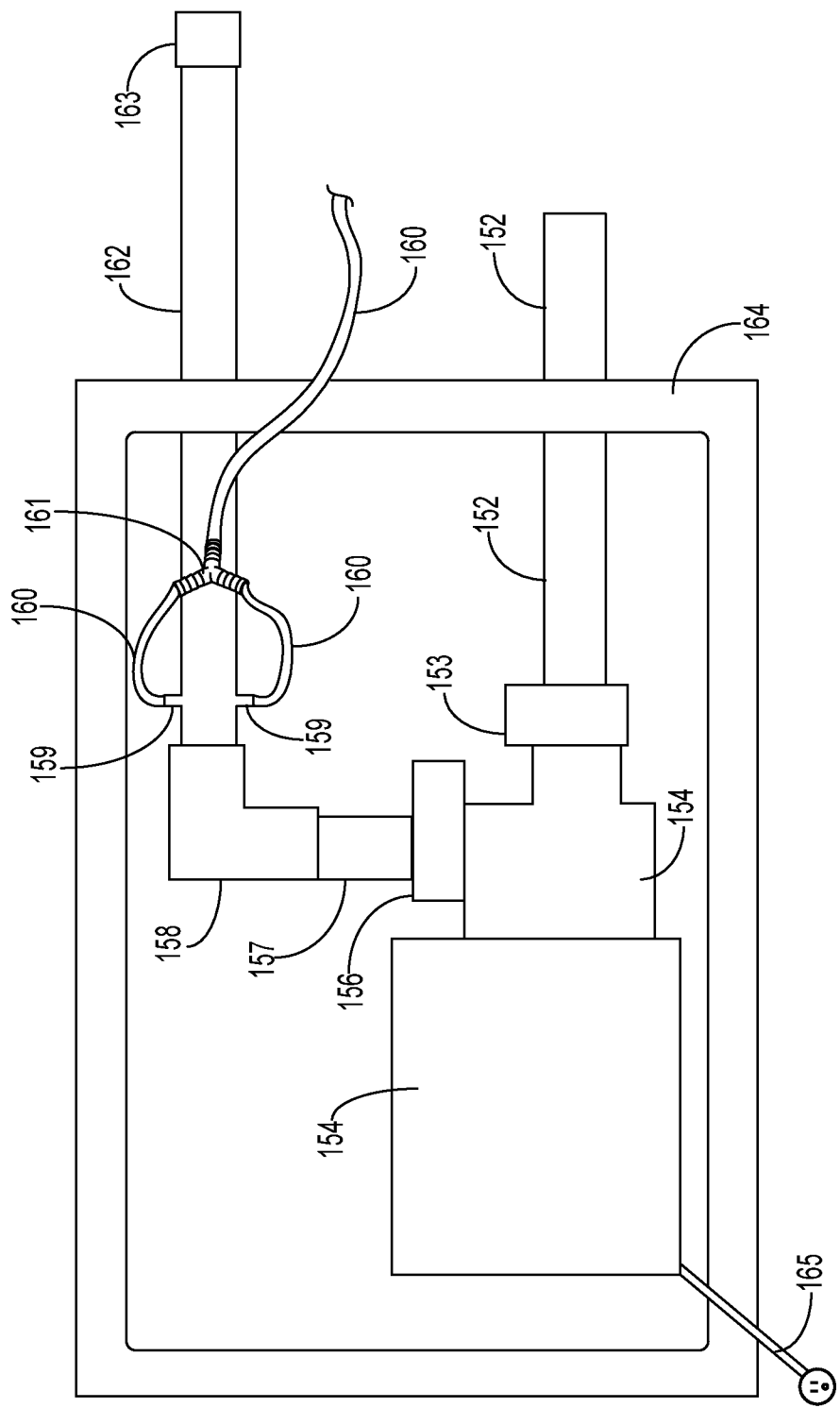
FIG. 12 illustrates an example of a pump/vane in accordance with various embodiments of the present disclosure.

FIG. 12 illustrates an example of a pump/vane. In some embodiments, such a pump/vane may be the same pump/vane referred to in FIG. 8 and/or FIG. 9. As illustrated in FIG. 12, liquid may flow from an external tank into a pipe 152 through a union joint 153 and into a pump 154. Once in the pump 154, liquid to be treated is pumped through a union 156, flows through a pipe 157, and flows through an elbow connection 158. Gas may be injected through stainless steel pins 159. The gas may be exposed to liquid upstream of vane in pipe. 162. Gas with a regulated flow from an external apparatus may flow through an air hose 160 and into the pipe housing vane 162. A coupling at a bottom end of the pipe housing vane 162 may connect to a tank. An outer shell housing 164 may provide encapsulation. A power source 165 may be connected to the pump 154 to provide power.

In some embodiments, a gas saturation controller may be included. The gas controller may provide a method to maintain gas saturation such as carbon dioxide in water is controlled by an automated pH controller system. The pH controller system may include an upper compartment and a lower component. The lower component may include a water pump attached to the helical vane with a check valve.

The component may, additionally or alternatively, include various elements, such as a Hanna instrument pH controller, a brass pressure switch, a 3-way solenoid actuator, a contactor, a motor starter, a socket DIN, and/or a relay plug-in. A pH probe may be immersed in a body of water, such as within a reservoir tank. The probe may continuously measure the pH. If the pH rises above a set point, the controller may determine that there is an adequate supply of carbon dioxide. The controller may then close a contact, which will then activate the motor and the carbon dioxide solenoid valve in order to allow carbon dioxide gas to flow from the carbon dioxide tank into the pipe housing the helical vane. This process may begin the dissolving of carbon dioxide and circulation in the reservoir. This process may continue until the pH probe measures the desired pH set point and opens the contact in the controller, which may then shut off the electricity to the motor starter contact, and the carbon dioxide solenoid may then stop the flow of gas and the pump. In order to prevent continuous operation of the water pump when no carbon dioxide is present from the carbon dioxide tank, and the pH controller is demanding carbon dioxide gas, a low-pressure switch may be used to prevent the operation of the water pump and the carbon dioxide solenoid.

As used herein, the term "liquid" refers to any liquid including, by way of example only, water or a water based solution; the term "gas" refers to any gas including, by way of example only, oxygen, carbon dioxide, argon or nitrogen. Moreover the term "mixing" refers to any contact of the liquid and the gas, and includes, by way of example only, infusion, injection, oxygenation, treating, processing, enhancing, and/or any other terms or results that can be obtained from contact of the liquid and the gas.

Figure 13A:
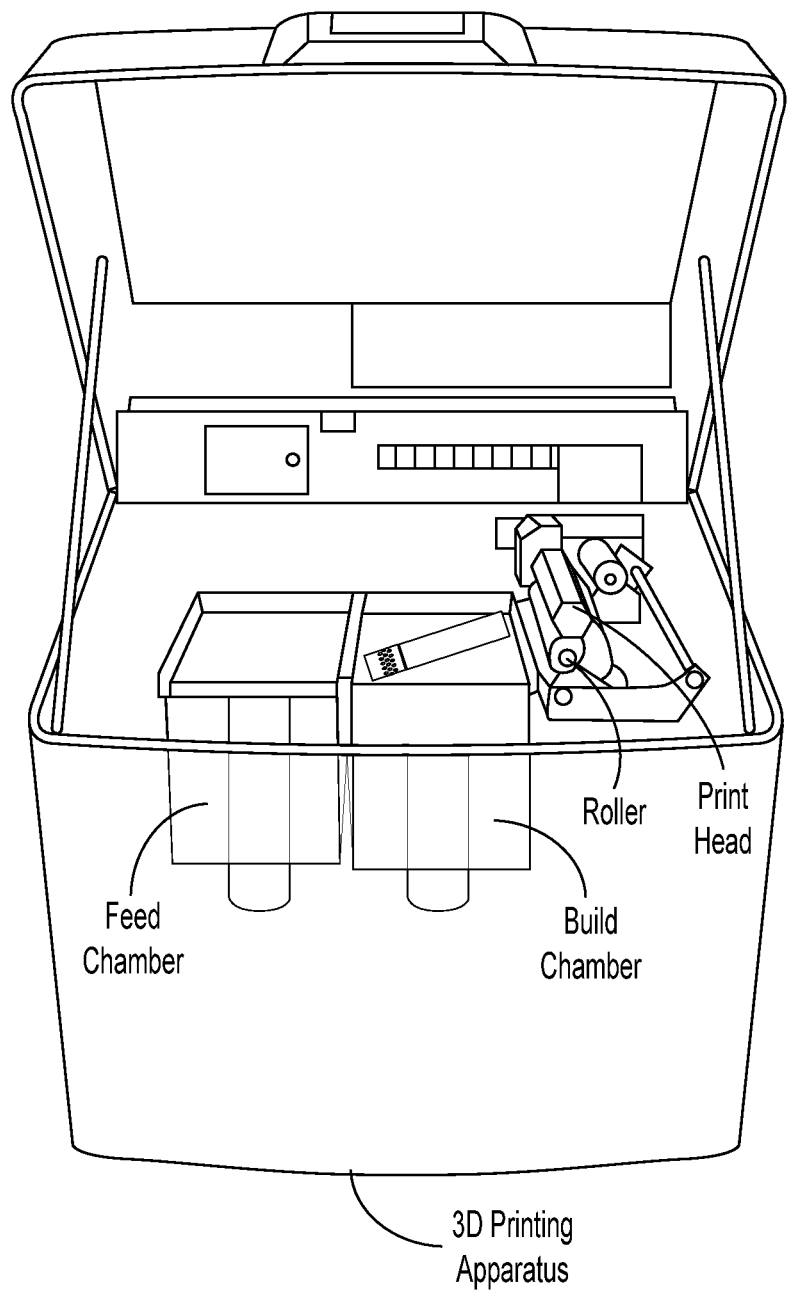
FIG. 13A illustrates an example of a three-dimensional (3D) printing apparatus in accordance with various embodiments of the present disclosure.
Figure 13B:
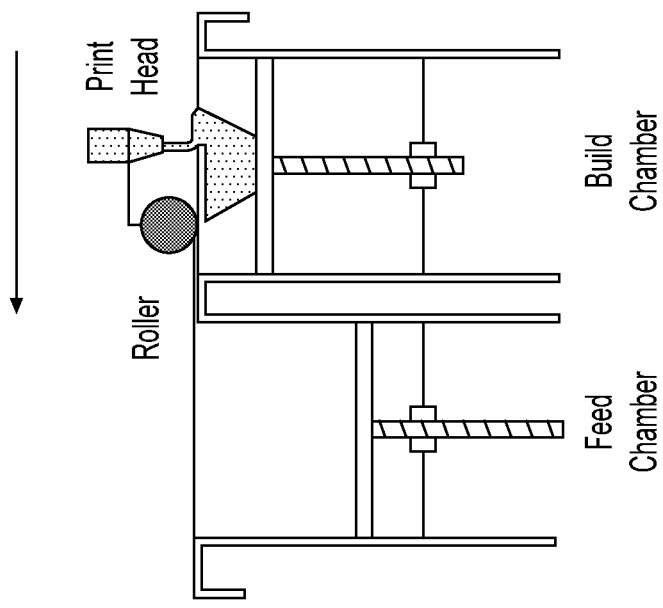
FIG. 13B illustrates an example of the 3D printing apparatus during a first stage in accordance with various embodiments of the present disclosure.

FIG. 13A illustrates an example of a three-dimensional (3D) printing apparatus in accordance with various embodiments of the present disclosure. FIG. 13B illustrates an example of the 3D printing apparatus during a first stage. FIG. 13B illustrates an example of the 3D printing apparatus during a second stage. 3D printing may be used as a direct manufacturing process as well as for rapid prototyping. 3D printing creates three-dimensional objects by inkjet printing liquid adhesive to join loose powder, which allows parts to be built very quickly and inexpensively. This technology may use ink-jet based processes. Multichannel print head may deposit liquid adhesive binder onto the top of a bed of powder object material. The powder may be bonded together in the areas where the adhesive is printed. The material used in this application may be calcium sulfate hemihydrate plaster based composite powder (ZP 130) and water-based binder (ZB 58).

Figure 13C:
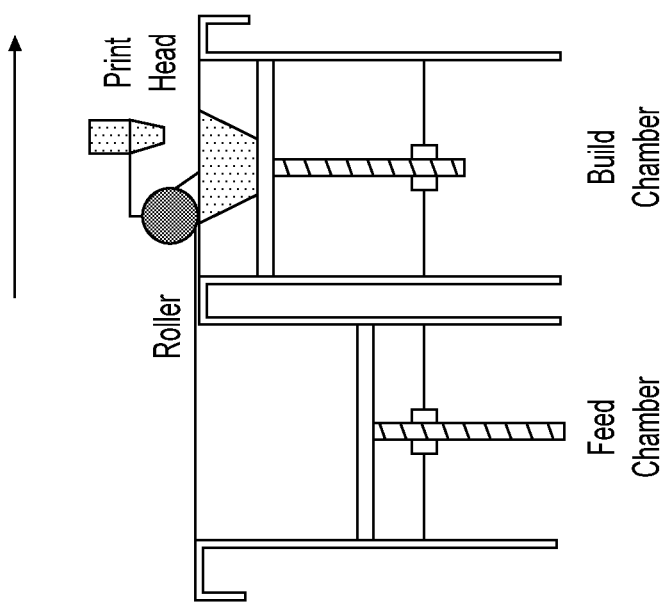
FIG. 13C illustrates an example of the 3D printing apparatus during a second stage in accordance with various embodiments of the present disclosure.

As illustrated in FIGS. 13A-13C, the 3D printing apparatus may include at least two chambers. A feed chamber may include the materials, which may be in the form of a powder, that will eventually form the 3D printed object. Some of the feed located inside of the feed chamber may be pushed upwards. A roller may dispose the feed from the feed chamber and towards the build chamber. The roller may be configured to apply a substantially uniform layer of the feed onto the build chamber. After the substantially uniform layer of the feed is positioned o the build chamber, the roller may move away from the build chamber. Afterwards, a print head may move on top of the substantially uniform layer of the feed. The print head may expel a binding element, or other similar compound, onto a designated portion of the substantially uniform layer of feed. The print head may spray the binding element at only the locations where the 3D printed object is to be formed. The 3D printed object is formed as the binding element is sprayed upon the corresponding region of the feed. Where the binding element is not sprayed by the print head, no 3D printed object is formed.

After the binding element is sprayed by the print head onto the designated area of the substantially uniform layer of feed, the bottom of the build chamber may be lowered in order to create some room for a new layer of feed. The new layer of feed is provided by moving the bottom of the feed chamber upwards. As described above, the roller is (again) moved across the build chamber in order to create a new substantially uniform layer of feed. As also described above, the print head can the move and spray the binding element on a particular portion of this new layer of feed. The foregoing process may be repeated until the 3D printed object is completed.

Although an example of a 3D printing apparatus is provided with reference to FIGS. 13A-13C, one of ordinary skill in the art will understand that various other 3D printing apparatuses may be used in accordance with various embodiments of the present disclosure without deviating from the scope of the present disclosure.

Figure 14:
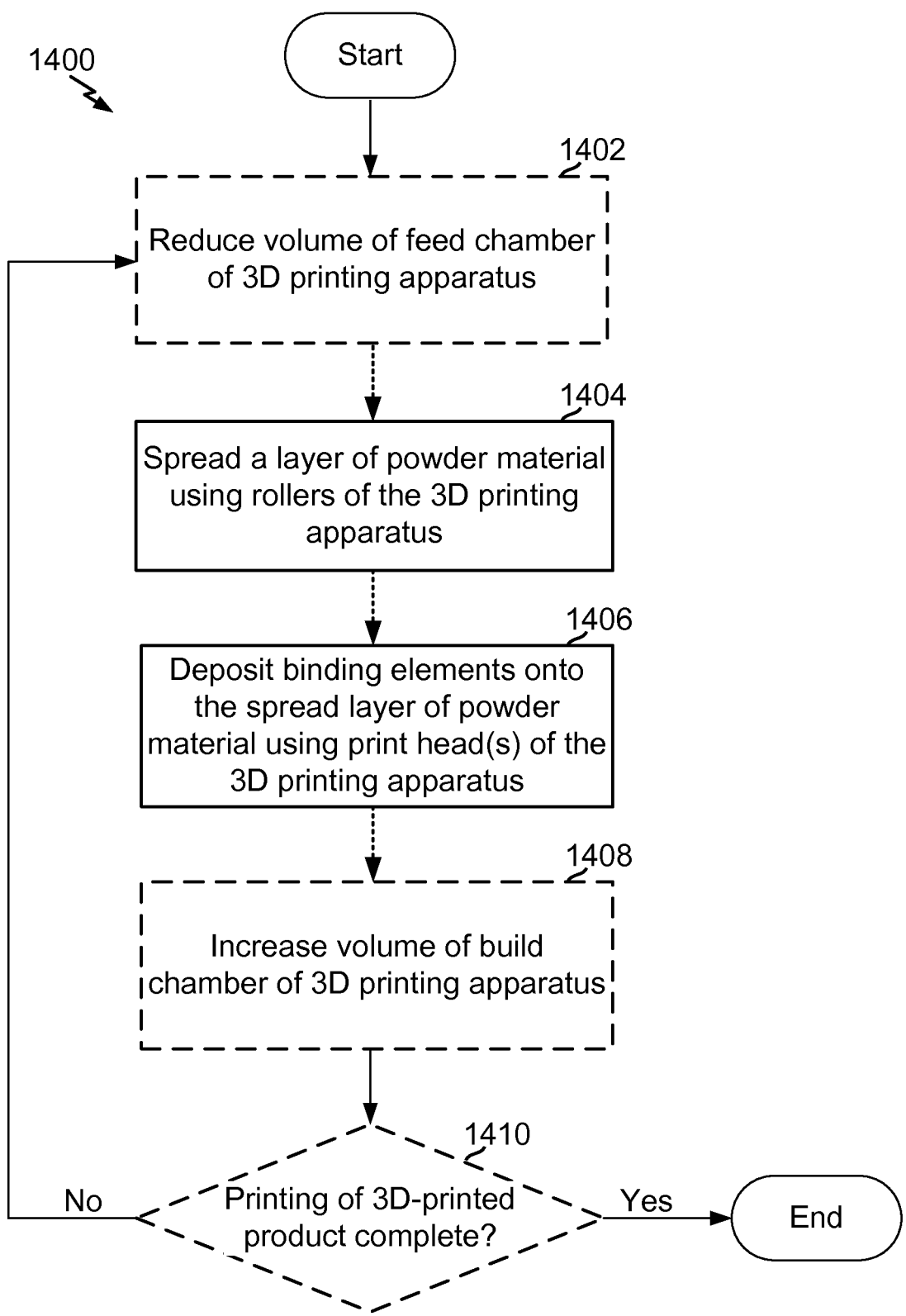
FIGS. 14 illustrates an example of a method and/or process in accordance with various embodiments of the present disclosure.

FIG. 14 illustrates an example of a method and/or process performed in accordance with the 3D printing apparatus. At block 1402, the 3D printing apparatus may reduce the volume of the feed chamber. For example, referring to FIGS. 13A-13C, the bottom of the feed chamber may be pushed upwards, thereby reducing the volume of the feed chamber. As a result of the reduction of the volume of the feed chamber, an amount of feed may be made available for rolling towards the direction of the build chamber.

At block 1404, the 3D printing apparatus may spread a layer of powder material using rollers. As illustrated in FIGS. 13A-13C, the feed may be rolled from the feed chamber towards the build chamber. The roller may form a substantially uniform layer of feed on the build chamber.

At block 1406, the 3D printing apparatus may deposit a binding element onto the spread layer of powder material using the print head(s). The binding element may cause the powder to congeal as a unitary object, which forms a portion of the 3D printed object.

At block 1408, the 3D printing apparatus may increase the volume of the build chamber. As illustrated in FIGS. 13A-13C, the bottom of the build chamber may be lowered, thereby increasing the volume of the build chamber. As a result of lowering the bottom of the build chamber, some room is created, which allows another layer of the powder to be provided on top of the preceding layer.

At block 1410, the 3D printing apparatus may determine whether the printing of the 3D printed object is complete. The printing is complete when no additional layers need to be added to the 3D printed object. However, if additional layers still need to be added to the 3D printed object, the method may proceed to block 1402, as described in greater detail above.

The methods and/or processes described with reference to FIG. 14 are provided for illustrative purposes and are not intended to limit the scope of the present disclosure. The methods and/or processes described with reference to FIG. 14 may be performed in sequences different from those illustrated therein without deviating from the scope of the present disclosure. Additionally, some or all of the methods and/or processes described with reference to FIG. 14 may be performed individually and/or together without deviating from the scope of the present disclosure. It is to be understood that the specific order or hierarchy of steps in the methods disclosed is an illustration of exemplary processes. Based upon design preferences, it is understood that the specific order or hierarchy of steps in the methods may be rearranged. The accompanying method claims present elements of the various steps in a sample order, and are not meant to be limited to the specific order or hierarchy presented unless specifically recited therein.

Figure 15:
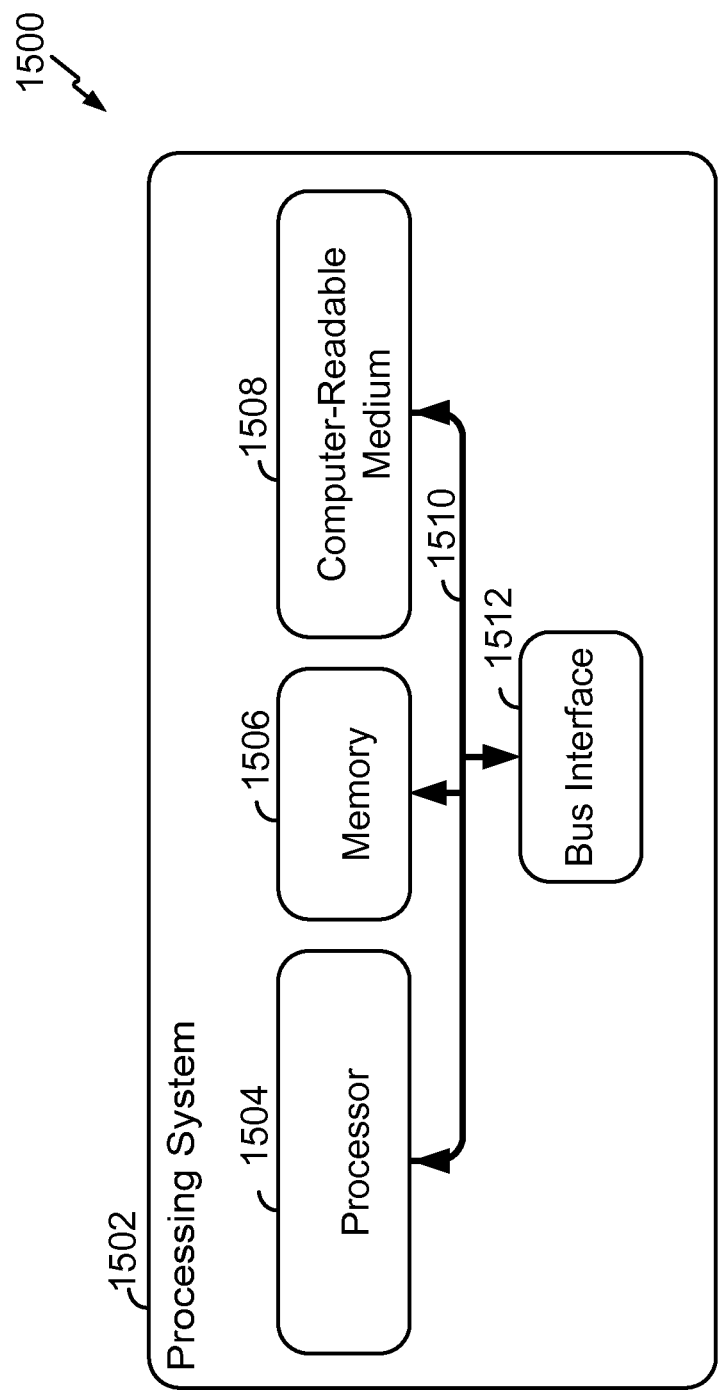
FIG. 15 illustrates an example of a hardware implementation in accordance with various embodiments of the present disclosure.

FIG. 15 illustrates an example of various hardware components of a processing system 1502 of the 3D printing apparatus. The processing system 1502 may include one or more processors 1504, a memory 1506, a computer-readable medium 1508, a bus 1510, and a bus interface 1512. The memory 1506, the one or more processors 1504, the computer-readable medium 1508, and the bus interface 1512 may be connected together via the bus 1510. The bus 1510 may also link various other circuits such as timing sources, peripherals, voltage regulators, transceivers, and/or power management circuits.

The processor 1504 may include various hardware components and/or software modules that can perform various functions and/or enable various aspects associated with controlling various operations of the processing system 1502 of the 3D printing apparatus. In some configurations, the processor 1504 provides the means for reducing the volume of the feed chamber of the 3D printing apparatus. In some configurations, the processor 1504 provides the means for spreading a layer of powder material using rollers of the 3D printing apparatus. In some configurations, the processor 1504 provides the means for depositing binding elements onto the spread layer of powder using rollers of the 3D printing apparatus. In some configurations, the processor 1504 provides the means for increasing the volume of the build chamber of the 3D printing apparatus. In some configurations, the processor 1504 provides the means for determining whether the printing of the 3D printed object is complete. The foregoing description provides a non-limiting example of the processor 1504 of the processing system 1502 of the 3D printing apparatus. Although various circuits have been described above, one of ordinary skill in the art will understand that the processor 1504 may also include various other processors and/or circuits that are in addition and/or alternative(s) to the processor 1504. Such other processors and/or circuits may provide the means for performing any one or more of the functions, methods, processes, features and/or aspects described herein.

The computer-readable medium 1508 may include various instructions. The instructions may include computer-executable code configured to perform various functions and/or enable various aspects described herein. The computer-executable code may be executed by various hardware components (e.g., the processor 1504) of the processing system 1502. The instructions may be a part of various software programs and/or software modules. In some configurations, the computer-readable medium 1508 may include instructions configured for reducing the volume of the feed chamber of the 3D printing apparatus. In some configurations, the computer-readable medium 1508 may include instructions configured for spreading a layer of powder material using rollers of the 3D printing apparatus. In some configurations, the computer-readable medium 1508 may include instructions configured for depositing binding elements onto the spread layer of powder using rollers of the 3D printing apparatus. In some configurations, the computer-readable medium 1508 may include instructions configured for increasing the volume of the build chamber of the 3D printing apparatus. In some configurations, the computer-readable medium 1508 may include instructions configured for determining whether the printing of the 3D printed object is complete. The foregoing description provides a non-limiting example of the computer-readable medium 1508 of the processing system 1502 of the 3D printing apparatus. Although various instructions (e.g., computer-executable code) have been described above, one of ordinary skill in the art will understand that the computer-readable medium 1508 may also include various other instructions that are in addition and/or alternative(s) to aforementioned instructions. Such other instructions may include computer-executable code configured for performing any one or more of the functions, methods, processes, features and/or aspects described herein.

The memory 1506 may include various memory modules. The memory modules may be configured to store, and have read therefrom, various values and/or information by the processor 1504. The memory modules may also be configured to store, and have read therefrom, various values and/or information upon execution of the computer-executable code included in the computer-readable medium 1508. In some configurations, the dimensions and measurements of the object to be 3D printed may be stored in the memory 1506. The processor 1504 may read such dimensions and measurements for each layer of the 3D printed object. One of ordinary skill in the art will also understand that the memory 1506 may also include various other memory modules. The other memory modules may be configured for storing information therein, and reading information therefrom, with respect to any of the features, functions, methods, processes, and/or aspects described herein.

One of ordinary skill in the art will also understand that the processing system 1502 may include alternative and/or additional elements without deviating from the scope of the present disclosure. In accordance with various aspects of the present disclosure, an element, or any portion of an element, or any combination of elements may be implemented with a processing system that includes one or more processors 1504. Examples of the one or more processors 1504 include microprocessors, microcontrollers, digital signal processors (DSPs), field programmable gate arrays (FPGAs), programmable logic devices (PLDs), state machines, gated logic, discrete hardware circuits, and other suitable hardware configured to perform the various functionality described throughout this disclosure.

Software shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise. The software may reside on the computer-readable medium 1508. The computer-readable medium 1508 may be a non-transitory computer-readable medium. A non-transitory computer-readable medium includes, by way of example, a magnetic storage device (e.g., hard disk, floppy disk, magnetic strip), an optical disk (e.g., a compact disc (CD) or a digital versatile disc (DVD)), a smart card, a flash memory device (e.g., a card, a stick, or a key drive), a random access memory (RAM), a read only memory (ROM), a programmable ROM (PROM), an erasable PROM (EPROM), an electrically erasable PROM (EEPROM), a register, a removable disk, and any other suitable medium for storing software and/or instructions that may be accessed and read by a computer. The computer-readable medium 1508 may also include, by way of example, a carrier wave, a transmission line, and any other suitable medium for transmitting software and/or instructions that may be accessed and read by a computer. The computer-readable medium 1508 may be embodied in a computer program product. By way of example and not limitation, a computer program product may include a computer-readable medium in packaging materials. Those skilled in the art will recognize how best to implement the described functionality presented throughout this disclosure depending on the particular application and the overall design constraints imposed on the overall system.

The foregoing description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." All structural and functional equivalents to the elements of the various aspects described throughout this disclosure that are known or later come to be known to those of ordinary skill in the art are expressly incorporated herein by reference and are intended to be encompassed by the claims.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language of the claims, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f), unless the element is expressly recited using the phrase "means for" or, in the case of a method claim, the element is recited using the phrase "step for."

The invention claimed is:

1. An apparatus for mixing a gas with a liquid, the apparatus comprising:
   a tube having a longitudinal axis and two ends, with a first end being a liquid input end and a second end being a liquid outlet end, the tube providing a first portion of a main fluid path that extends through the apparatus;
   a helical vane disposed inside the tube, dividing the first portion of the main fluid path into two fluid path regions;
   a tubular structure extending from the first end of the tube and located upstream of the helical vane and aligned with the longitudinal axis of the tube, the tubular structure providing a second portion of the main fluid path and having a sidewall configured to allow gas to flow there through at a plurality of locations around a circumference of the tubular structure;
   a joint pipe having an inner wall defining an inner diameter sized to receive the tubular structure and the first end of the tube, and to provide an annular space between the inner wall and the sidewall of the tubular structure;
   a gas injection port associated with the joint pipe and located upstream of the helical vane, the gas injection port adapted to inject gas into the annular space, through the sidewall of the tubular structure and into the second portion of the main fluid path provided by the tubular structure; and
   a ring structure located upstream of the helical vane and downstream of the gas injection port and the tubular structure, the ring structure extending around an outer wall of the tube and positioned between the inner wall of the joint pipe and the outer wall of the tube to define a downstream end of the annular space.

2. The apparatus of claim 1, wherein the tube and the helical vane are a single three-dimensional (3D) printed component.

3. The apparatus of claim 1, further comprising a gas supply, wherein the gas comprises oxygen.

4. The apparatus of claim 1, further comprising a gas supply, wherein the gas comprises carbon dioxide.

5. The apparatus of claim 1, further comprising a liquid supply, wherein the liquid comprises water.

6. The apparatus of claim 1, wherein the helical vane is a 3D printed component.

7. The apparatus of claim 1, further comprising a second helical vane disposed downstream from the helical vane.

8. The apparatus of claim 1, further comprising a pipe, wherein the tube with the helical vane is disposed within the pipe.

9. The apparatus of claim 1, wherein the tubular structure is integral with the end of the tube, and the plurality of locations around a circumference of the tubular structure are provided by holes that extend through the sidewall of the tubular structure.

10. The apparatus of claim 1, wherein the tubular structure is a porous membrane having an inner wall in snug contact with the first end of the tube, and the plurality of locations around a circumference of the tubular structure are provided by pores that extend through the sidewall.

11. The apparatus of claim 1, wherein the gas injection port is at least partially aligned with the sidewall of the tubular structure.

12. The apparatus of claim 1, wherein the tube and the helical vane are unitary with each other.

13. The apparatus of claim 1, wherein the annular space between the inner wall of the joint pipe and the sidewall of the tubular structure extends along the entirety of the tubular structure.

* * * * *